United States Patent
Abelbeck

(10) Patent No.: US 10,617,570 B2
(45) Date of Patent: Apr. 14, 2020

(54) WOUND CLOSING BANDAGE

(71) Applicant: Kevin Gene Abelbeck, Fort Collins, CO (US)

(72) Inventor: Kevin Gene Abelbeck, Fort Collins, CO (US)

(*) Notice: Subject to any disclaimer, the term of this patent is extended or adjusted under 35 U.S.C. 154(b) by 680 days.

(21) Appl. No.: 15/383,665

(22) Filed: Dec. 19, 2016

(65) Prior Publication Data
US 2018/0168871 A1    Jun. 21, 2018

(51) Int. Cl.
*A61F 13/02* (2006.01)
*A61F 13/00* (2006.01)

(52) U.S. Cl.
CPC ........ *A61F 13/0259* (2013.01); *A61F 13/025* (2013.01); *A61F 13/0233* (2013.01); *A61F 13/0243* (2013.01); *A61F 2013/0028* (2013.01); *A61F 2013/00119* (2013.01); *A61F 2013/00153* (2013.01)

(58) Field of Classification Search
CPC .............. A61F 15/006; A61F 13/0259; A61F 13/0243; A61F 13/025
See application file for complete search history.

(56) References Cited

U.S. PATENT DOCUMENTS

| | | | |
|---|---|---|---|
| 380,093 A * | 3/1888 | Cruice et al. ........... | A01L 15/00 606/212 |
| 2,387,131 A | 10/1945 | Fernandez | |
| 2,762,371 A * | 9/1956 | Guio .................... | A61B 17/085 606/216 |
| 2,818,865 A | 1/1958 | Jacoby | |
| 3,698,395 A | 10/1972 | Hasson | |
| 3,971,384 A | 6/1976 | Hasson | |
| 4,038,989 A | 7/1977 | Romero-Sierra et al. | |
| 4,141,363 A * | 2/1979 | James ................. | A61B 17/085 606/216 |
| 4,275,721 A | 6/1981 | Olson | |
| 4,418,822 A | 12/1983 | Dotta | |
| 4,646,731 A | 3/1987 | Brower | |
| 4,715,366 A * | 12/1987 | Teeple .................. | A61B 90/04 128/849 |
| 4,732,146 A | 3/1988 | Fasline et al. | |
| 4,815,468 A | 3/1989 | Annand | |
| 4,909,243 A | 3/1990 | Frank et al. | |
| 4,950,282 A * | 8/1990 | Beisang ............... | A61B 17/085 606/216 |
| 4,969,880 A | 11/1990 | Zamierowski | |
| 5,086,763 A | 2/1992 | Hathman | |
| 5,158,555 A | 10/1992 | Porzilli | |

(Continued)

*Primary Examiner* — Richard G Louis

(57) ABSTRACT

A wound closing bandage may include a first member and a second member, each with a first end and a second end. The first member and the second member may be positioned adjacent to one another and secured in an optimal initial position with respect to one another by way of a locator tab. The first ends of the first member and the second member may be positioned on and secured to the skin of a user and adjacent to the edges of an open wound or incision, the bandage location may be guided by a locator line. The second ends of the first member and the second member may be pulled apart from one another, severing or detaching the locator tab and pulling the open wound closed. The second ends may then be secured to the skin and/or top of the first ends already secured to the skin.

20 Claims, 19 Drawing Sheets

(56) References Cited

U.S. PATENT DOCUMENTS

| | | |
|---|---|---|
| 5,170,781 A | 12/1992 | Loomis |
| 5,176,703 A | 1/1993 | Peterson |
| 5,263,970 A | 11/1993 | Preller |
| 5,336,209 A | 7/1994 | Porzilli |
| 5,449,340 A | 9/1995 | Tollini |
| 5,534,010 A | 7/1996 | Peterson |
| 5,772,623 A | 6/1998 | Conte |
| 6,329,564 B1 | 12/2001 | Lebner |
| 6,664,435 B2 | 12/2003 | Masini |
| 6,822,133 B2 | 3/2004 | Lebner |
| 6,831,205 B2 | 12/2004 | Lebner |
| 7,012,170 B1 | 3/2006 | Tomaioulo |
| 7,354,446 B2 | 4/2008 | Lebner |
| 7,414,168 B2 | 8/2008 | Lebner |
| 7,511,185 B2 | 3/2009 | Lebner |
| 7,696,399 B2 | 4/2010 | Rogers |
| 7,838,718 B2 | 11/2010 | Lebner |
| 8,157,839 B2 | 4/2012 | Riskin et al. |
| 8,283,514 B2 | 10/2012 | Baschnagel |
| 2002/0042600 A1* | 4/2002 | Datta ............... A61F 13/49014 604/385.13 |
| 2004/0193216 A1* | 9/2004 | Deutsch ............. A61B 17/085 606/216 |
| 2005/0080453 A1* | 4/2005 | Lebner ............... A61B 17/085 606/216 |
| 2012/0221044 A1* | 8/2012 | Archibald ............ A61B 17/08 606/214 |
| 2012/0226306 A1* | 9/2012 | Jackson ............... A61F 13/00 606/201 |

\* cited by examiner

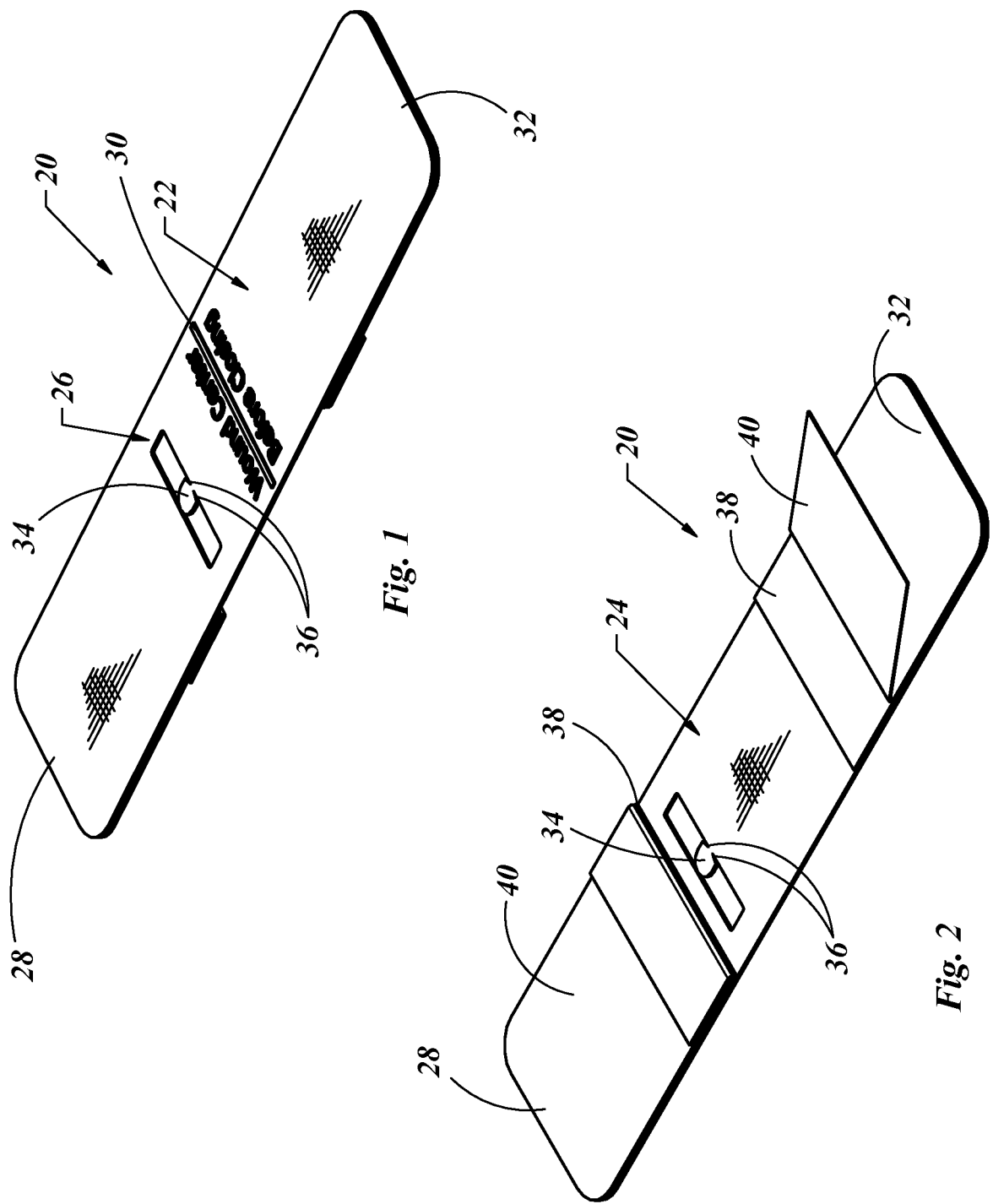

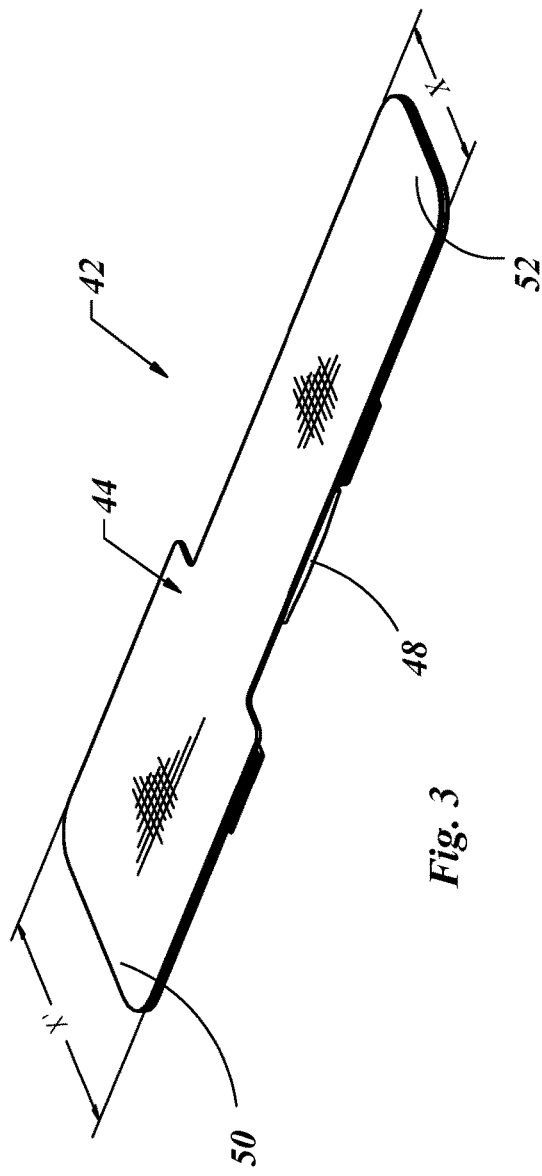
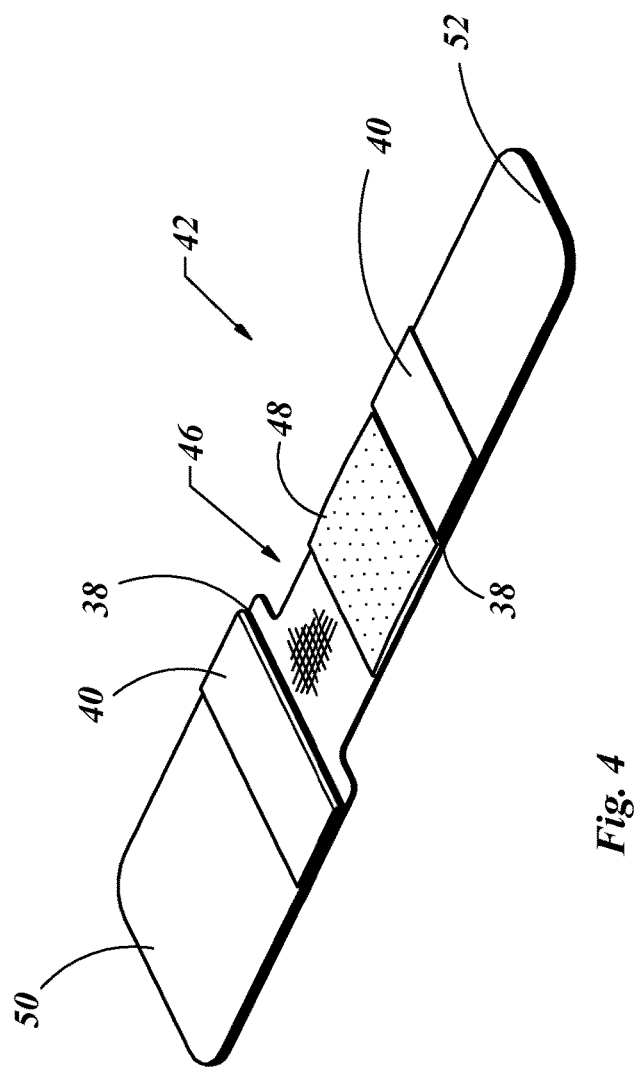

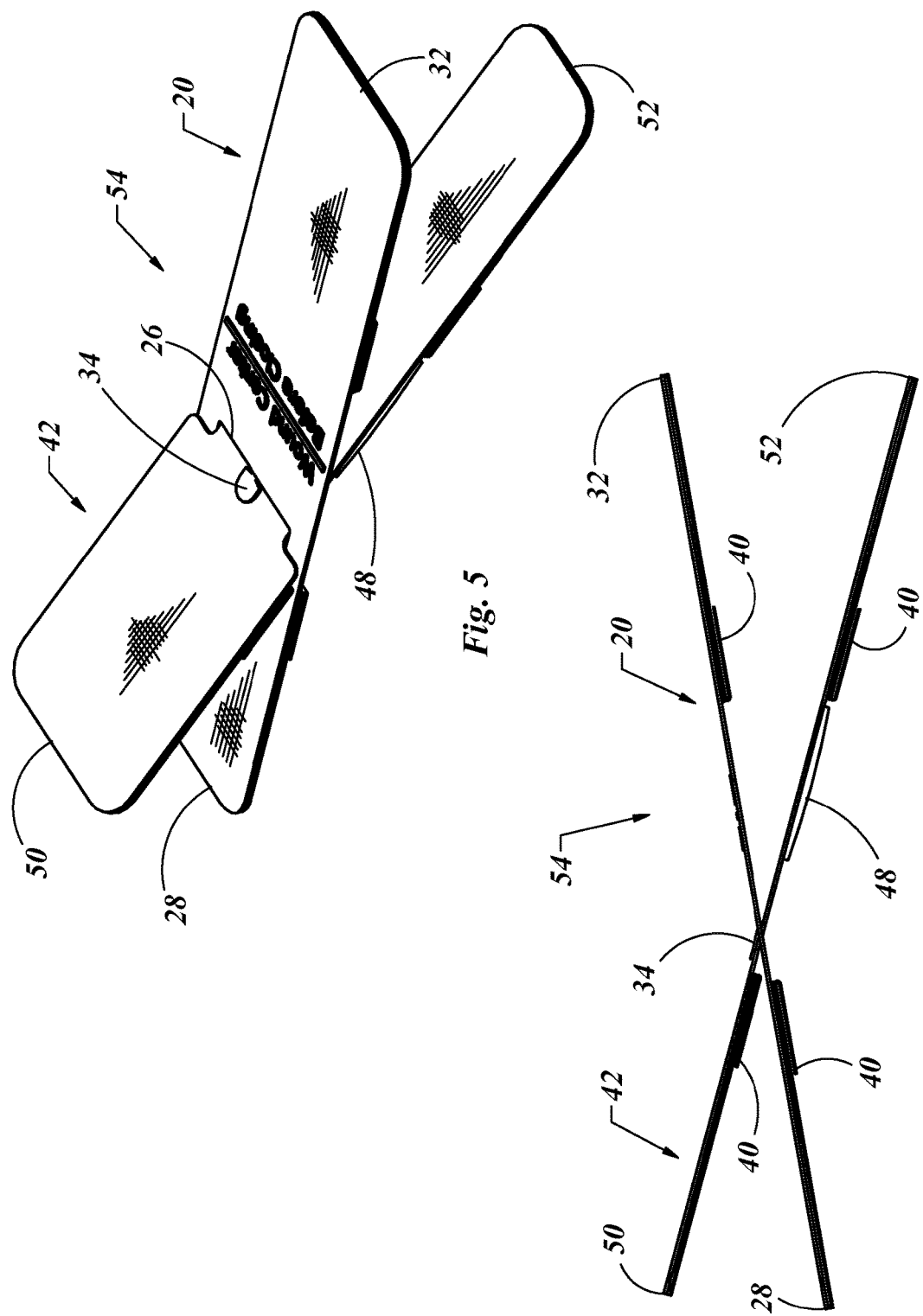

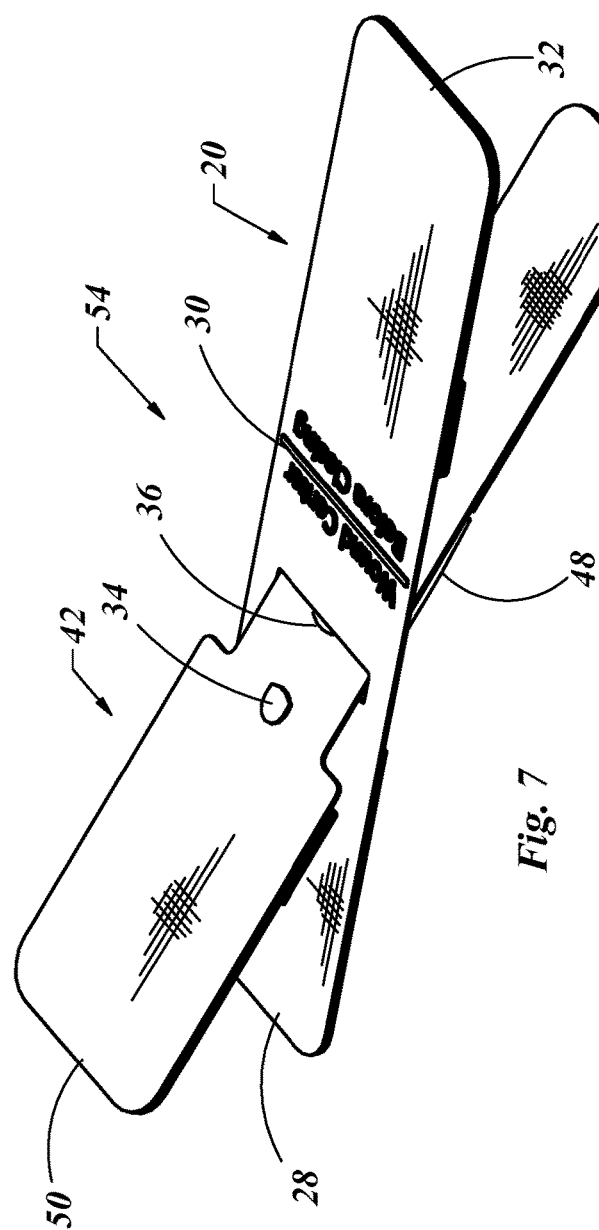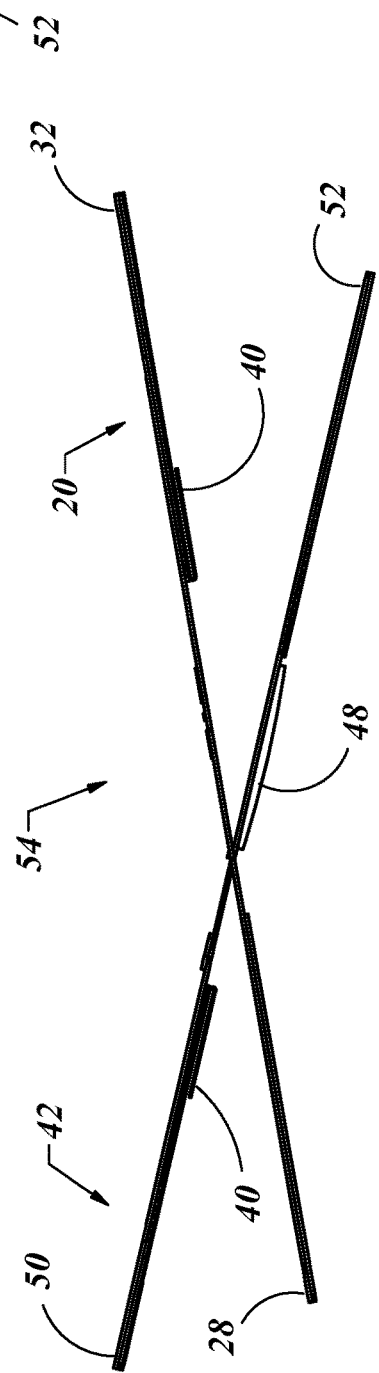

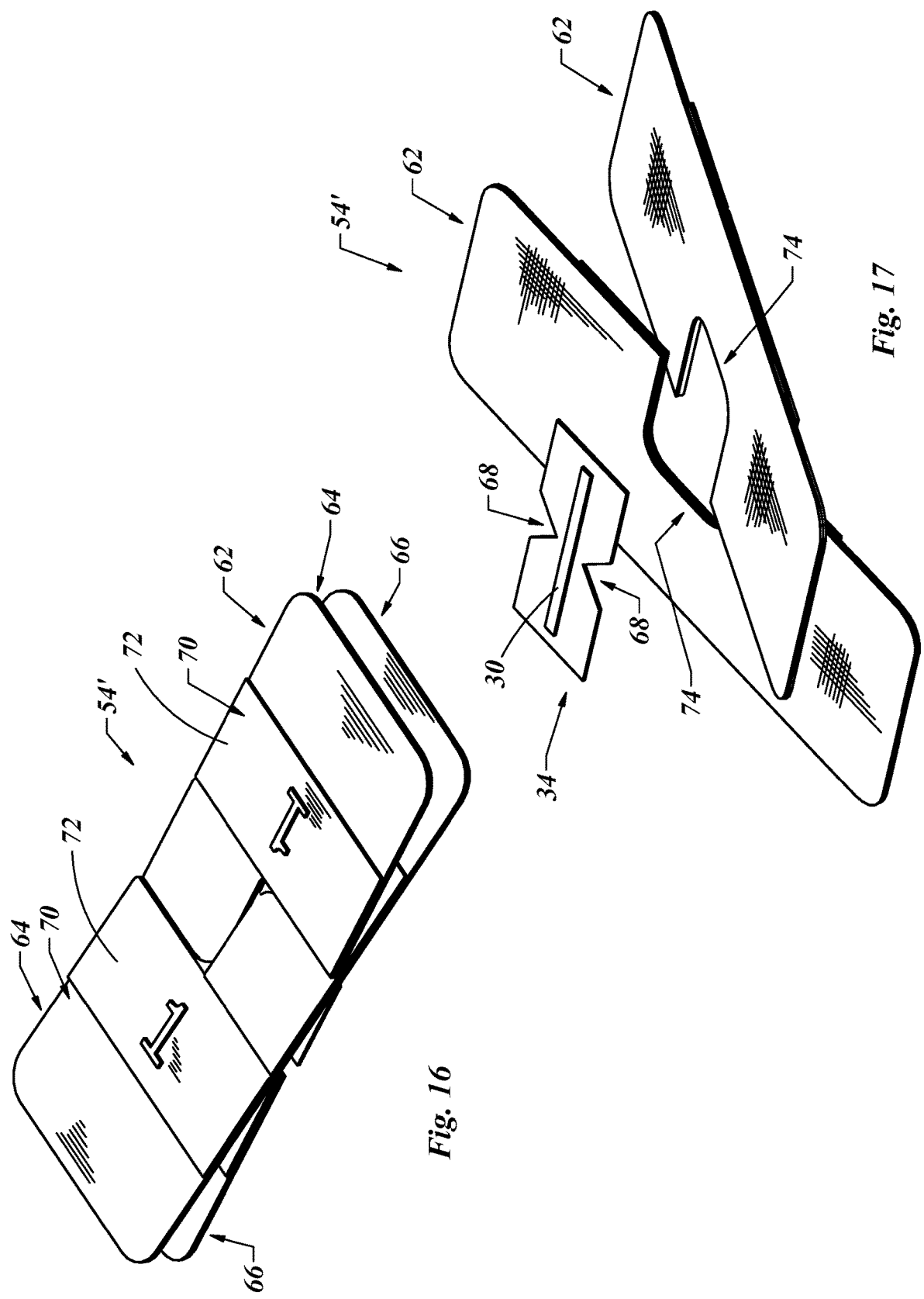

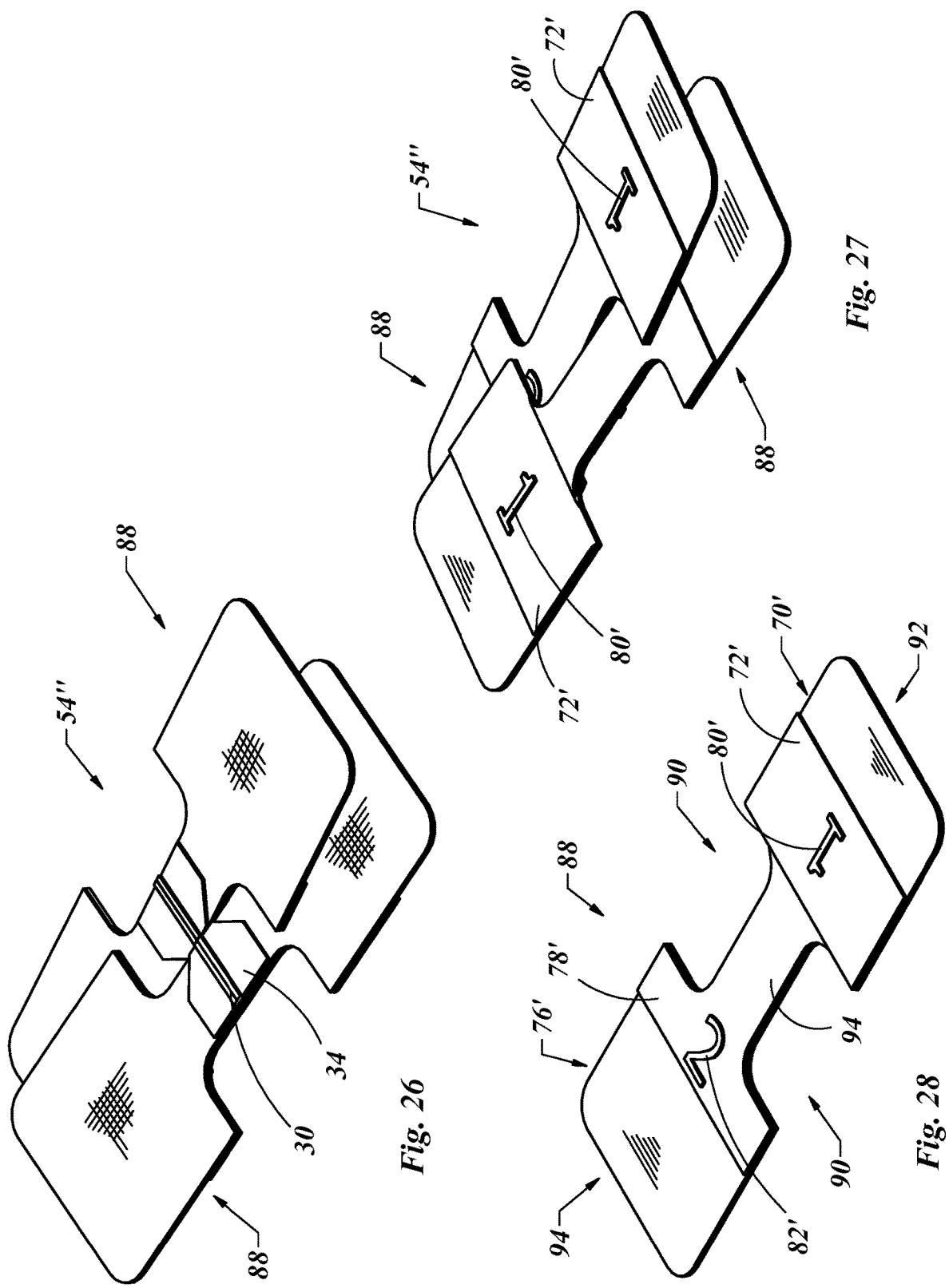

WOUND CLOSING BANDAGE

CROSS-REFERENCE TO RELATED APPLICATION DATA

Priority is claimed under 35 U.S.C. § 119(e) to U.S. Provisional Application No. 62/387,419, filed on Dec. 24, 2015, which is incorporated by reference herein.

FIELD OF THE INVENTION

The present invention generally relates to bandages and, more particularly, to bandages used to close open wounds without the use of sutures.

BACKGROUND OF THE INVENTION

A simple cut, if deep enough, in the human skin may result in a trip to the emergency room to have the wound stitched back together. This is commonly done through the use of sutures and a needle to close the wound such that the skin on one side of the wound is now in contact with the skin on the opposite side of the wound. The process of closing the wound accelerates the healing process, allows the tissue to knit back together, minimizes the likelihood of infection and reduces scaring. The downside in the process of closing the wound by "stitching" or "suturing" is that it requires a degree of skill, typically only found in medical professionals. If a medical professional is not readily available, the option to suture the wound closed is likely not available, as few people without this medical training would be competent or able to perform the task, even at a minimal level.

A second limitation to the process of suturing a wound closed is physiological and at the same time philosophical. The physiological aspect relates to the pain that would be experienced by the wounded person each time the needle is inserted into the skin surrounding the open wound, as is necessary to pass the suture material through the skin. A medical professional may have access to a local anesthetic or other numbing agent used to block the pain signals that would normally be present with every stick of the needle. If a medical professional, or the anesthetic are not available, the pain associated with each poke of the needle may be very unpleasant, to the point of intolerable to many people. From a philosophical standpoint, is seems counter intuitive to create a series of holes in a wound for the sole purpose of closing the "hole" in the skin, which is in fact the wound.

PRIOR ART

Attempts have been made to come up with a solution which enables a user to close an open wound without using traditional sutures. The vast majority of these attempts have resulted in products which are complicated and very expensive to manufacture, if in fact useful at all. One attempt which has been shown to be viable is U.S. Pat. No. 7,511,185 to Lebner. This patent discloses a system which is clearly limited to use by a medical practitioner, and also includes several limitations that have been overcome in the present invention disclosed herein.

The disclosure of the Lebner '185 patent details a bandage including two pulling elements on one end, each with a flat flexible component on the second end, connected by a series of elongated connectors which are interwoven in that the elongated connectors pass through a series of slots, those being the space between the elongated connectors. The intended use is that the flat flexible components are adhered to the skin, one on either side of the open incision in the patient. The pulling elements are then pulled away from one another, thus pulling the flat flexible components toward one another, applying force to close the open wound. The elongated connectors are then adhered to the top of the flat flexible components and the pulling elements are then cut off and discarded. The width of the elongated connectors is intentionally less than the space through which they protrude to interlace the two elements of the bandage. This is intentional in that as stated by Lebner in U.S. Pat. '185" . . . One of the two flat flexible components is applied to the skin before the other flat flexible complement. Following application, this flat flexible complement is not easily removed and repositioned. Therefore, having sufficient spacing between the elongated connectors is important to facilitate fine adjustment of the unattached flat flexible complement relative to the attached flat flexible complement." This illustrates a level of skill required in placing the elements on the skin, positioning them properly and then pulling evenly to close the wound with a minimal amount of twist or shear force applied to the open surfaces of each side of the wound.

A second feature of Lebner '185 is that his invention is preferred to be made of a "substantially inelastic poly metric material. Alternatively, they may be produced from elastic material which is reinforced with an inelastic structural complement thereby rendering the device substantially inelastic." As further stated: "the flat flexible elements, elongated connectors and pulling elements are produced from sheet stock (e.g., plastic sheet stock)." Therefore, it is clear that the Lebner '185 patent intends to follow the example used by a traditional nylon suture, which his manufactured of a material with a very high modulus of elasticity and therefore is very rigid.

As previously noted in the general use of Lebner '185, the pulling elements are removable following application of the bandage to the skin. This is further explained in the statement: "This feature minimizes the bandage size following application to the patient. This decrease in the overall size of the bandage reduces the chance that a portion of the bandage may be caught, for example, on clothing or a pillow. Such an occurrence could tend to pull the bandage away from the skin thereby causing the wound or incision to open."

Another important detail in Lebner '185 is that only a portion of the elongated connector includes an adhesive. This is clarified as: "care is taken during the design and manufacturing process to ensure that adhesive is not applied [emphasis added] to an elongated connector in the location which would result in contact between the adhesive and the wound." It is clear that the intention is not to adhere the skin directly adjacent to the wound edges, even when the wound is closed. Overcoming the immediate shear forces applied to the skin is therefore not taken into account by Lebner '185.

SUMMARY OF THE INVENTION

The present invention may provide a wound closing bandage with a female portion and a male portion. The female portion may include a slot adapted to receive a portion of the male portion. The female portion may also include a locator tab, which may be present near the slot. The locator tab may be secured to a top side of the male portion when the male portion is assembled with the female portion by way of the slot of the female portion. The locator tab may be secured to the male portion so as to locate the male portion relative to the female portion prior to use of the wound closing bandage. The female portion may also include an indicator line on an upper side thereof. The female portion and the male portion may both include adhesive pads which may be located on two distal ends of each of the male portion and the female portion. The adhesive pads may each include a removable adhesive cover, which may be used to prevent the adhesive pads from adhering to a surface not intended by a user.

The wound closing bandage may be positioned on the skin of a user with an open wound. The indicator line may be positioned over the center of the open wound. The adhesive covers may be removed from the adhesive pads of the lower ends or "base ends" of the assembled wound closing bandage. The base ends of the wound closing bandage may be fastened to the skin of the user on either side of the wound by the adhesive pads, the center of the wound substantially coincident with the indicator line of the wound closing bandage. The user may remove the adhesive covers from the upper ends of the wound closing bandage or the "pull ends". This may expose the adhesive pads of the pull ends of the wound closing bandage. The user may apply tension to the pull ends, moving them away from one another. This action may separate the locator tab of the female portion from the male portion, or remove the locator tab from the male portion. Either way, the male portion is allowed to move through the slot of the female portion. This action of moving the pull ends away from one another may pull the base ends and the skin attached to the base ends toward one another, thus closing the edges of the open wound toward one another. The user then may fasten the pull ends of the wound closing bandage over the base ends of the bandage and any exposed skin, thus closing the wound and maintaining the wound in a closed position.

An alternative embodiment of the invention may include two substantially identical U-shaped members or I-shaped members, each with an adhesive backing. The U-shaped or I-shaped members may be comprised of an elastomeric material with a modulus of elasticity equal to or less than that of human skin. The two U-shaped or I-shaped members may be assembled such that the reduced section center portions are received adjacent one another with a first end of each U-shaped or I shaped member positioned under a second end of the other U-shaped or I-shaped member. A location tab may be provided across the reduced section of the interlocked U-shaped or I-shaped members so as to position each of the U-shaped or I-shaped members relative to the other in a desired starting position. The lower first ends may be secured to the skin of a user. The second ends, positioned above the first ends, may be pulled apart from one another, separating the location tab. The second ends may now be secured to the top of the first ends and any exposed skin of the user beyond the far portions of the first ends.

For purposes of summarizing the invention and the advantages achieved over the prior art, certain advantages of the invention have been described herein above. Of course, it is to be understood that not necessarily all such advantages can be achieved in accordance with any particular embodiment of the invention. Thus, for example, those skilled in the art will recognize that the invention can be embodied or carried out in a manner that achieves or optimizes one advantage or group of advantages as taught herein without necessarily achieving other advantages as may be taught or suggested herein.

All of these embodiments are intended to be within the scope of the invention herein disclosed. These and other embodiments of the present invention will become readily apparent to those skilled in the art from the following description of the preferred embodiments and drawings, the invention not being limited to any particular preferred embodiment(s) disclosed.

BRIEF DESCRIPTION OF THE DRAWINGS

Embodiments of the present invention will now be described, by way of example only, with reference to the following drawings, in which:

FIG. 1 is an isometric top view of a female portion of a wound closing bandage, the bandage produced in accordance with the present invention.

FIG. 2 is an isometric bottom view of the female portion of the wound closing bandage of FIG. 1, showing one of the adhesive covers being partially removed.

FIG. 3 is an isometric top view of a male portion of a wound closing bandage, the bandage produced in accordance with the present invention.

FIG. 4 is an isometric bottom view of the male portion of the wound closing bandage shown in FIG. 3.

FIG. 5 is an isometric view of a wound closing bandage in an assembled state, prior to contraction of the base ends of the bandage.

FIG. 6 is a side view of the assembled wound closing bandage shown in FIG. 5.

FIG. 7 is an isometric view of a wound closing bandage in an assembled state, after the contraction of the base ends of the bandage, as would be done to close a wound.

FIG. 8 is a side view of the assembled wound closing bandage shown in FIG. 7.

FIG. 16 is an isometric view showing the underside, or side closest to the skin, of the wound closing bandage of FIG. 14.

FIG. 17 is an isometric of the wound closing bandage of FIG. 14 shown in a partially disassembled state.

FIG. 26 is a top isometric view of an alternative embodiment of the wound closing bandage wherein the formerly U-shaped member is now an I-shaped element.

FIG. 27 is a bottom isometric view of an alternative embodiment of the wound closing bandage wherein the formerly U-shaped member is now an I-shaped element.

FIG. 28 is a bottom isometric view of a single I-shaped element of the wound closing bandage of FIG. 26.

DETAILED DESCRIPTION OF THE INVENTION

Figure 9:
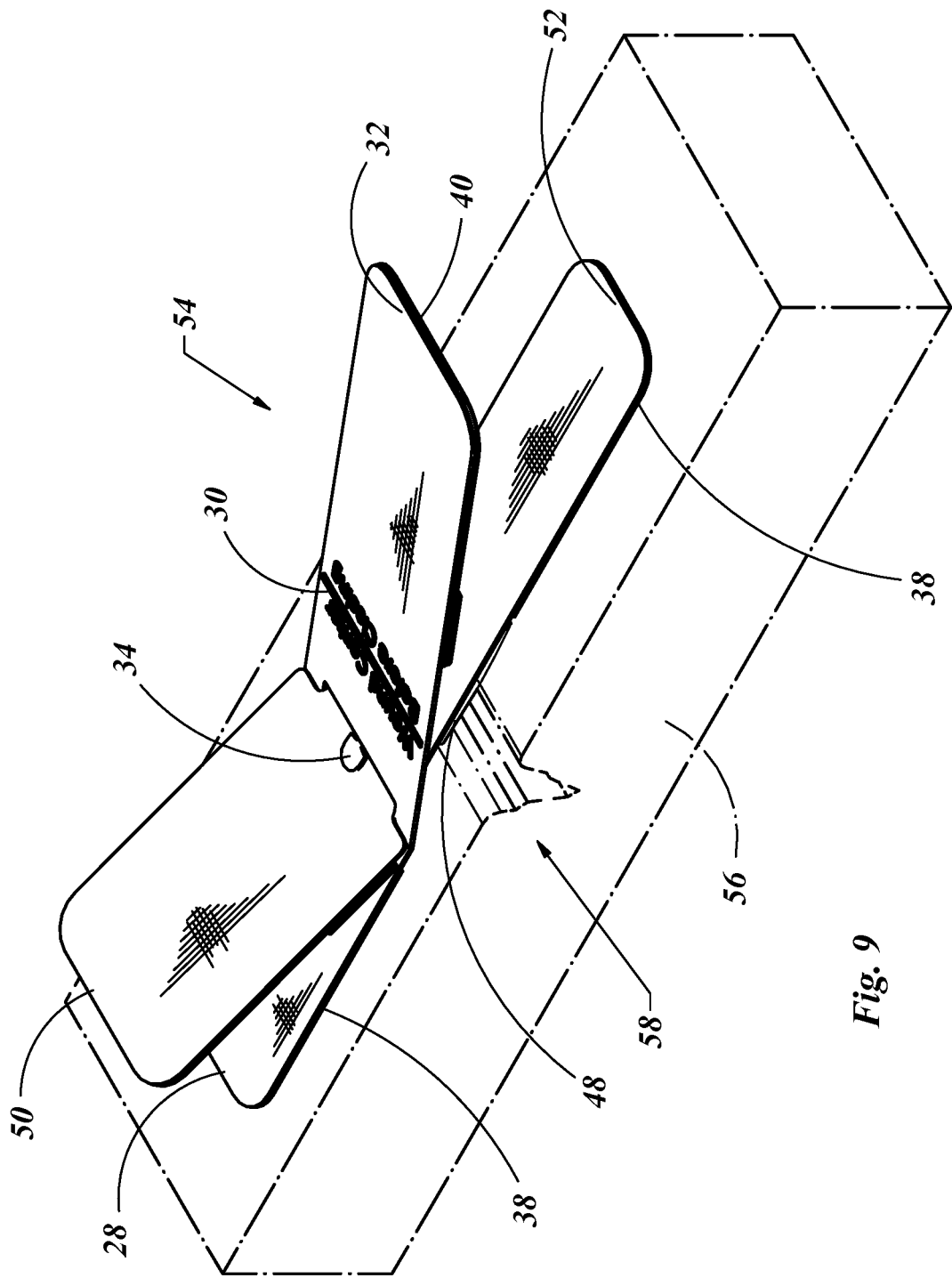
FIG. 9 is an isometric view of the wound closing bandage of FIG. 5 as it may be positioned over the open wound with the base ends of the male portion and the female portion adhered to the skin of a user.

With reference to the illustrative drawings, and particularly to FIG. 1, there is shown a first embodiment of a wound closing bandage including a female portion 20 of the wound closing bandage. The female portion 20 of the wound closing bandage may include an upper side 22, as shown in FIG. 1, and a lower side 24, as shown in FIG. 2. The female portion 20 may include a slot 26 substantially centered along the width of the female portion 20 and closer to a first end 28 and a second end 32 of the female portion 20. An indicator line 30 may also be located on the upper side 22 of the female portion 20. The indicator line 30 may be closer to the second end 32 than to the first end 28 of the female portion 20. A locator tab 34 may be continuous with the upper side 22 of the female portion 20. The locator tab 34 may be located within the slot 26, and may include a relief 36 such that if enough tension is placed on the locator tab 34 it may tear loose from the female portion 20.

The female portion 20 may include an adhesive patch 38 adjacent to the first end 28 and the second end 32 of the female portion 20, as is shown in FIG. 2. An adhesive cover 40 may be placed over each of the adhesive patches 38, which may prevent the adhesive patches 38 from inadvertently adhering to a structure not intended by a user.

The female portion 20 may work in combination with the male portion 42, as shown in FIGS. 3 and 4. The male portion 42 may include a top side 44 and a bottom side 46. The male portion 42 may include a section wherein the minor width (x) is less than the major width (x') of the male portion 42. The minor width (x) may be slightly less than the width of the slot 26 of the female portion 20, in FIG. 1. An intended purpose of this will become apparent later in the disclosure. The bottom side 46 of the male portion 42 may include more than one adhesive patch 38, each protected by adhesive cover 40. This may be used in a similar fashion to that as shown and described previously for the female portion 20. In addition, a wound pad 48 may be provided and located between the first end 50 of the male portion 42 second end 52 of the male portion 42. The male potion 42 and the female portion 20 may be die cut from any suitable material including elastic rubber, latex, cotton, plastic, woven synthetic material or ETS, used in many adhesive bandages.

With reference to FIGS. 5 and 6, the male portion 42 may be inserted into the slot 26 of the female portion 20, in combination creating a wound closing bandage 54. The locator tab 34 of the female portion 20 may include an adhesive or be otherwise bonded to the male portion 42 such that the combination of the female portion 20 and the male portion 42 comprise a single wound closing bandage 54. When the locator tab 34 is bonded to the male portion 42, the first end 28 of the female portion 20 may be proximal to the first end the 50 of the male portion, and the second end 32 of the female portion 20 may be proximal to the second end 52 of the male portion 42 of the wound closing bandage 54. This orientation of the wound closing bandage 54 may be the starting position of the wound closing bandage 54. This is an example of how it may be placed on the skin of a user. The relative orientation of the female portion 22 and the male portion 42 to be in the form of an "X" is only shown for illustrative purposes. The wound closing bandage 54 may lay flat with the first end 50 of the male portion 42 on top of the first end 28 of the female portion 20 and the second end 32 of the female portion 20 on top of the second end 52 of the male portion 42. The first end 28 of the female portion 20 and the second end 52 of the male portion may be considered the "base ends" in that these ends contact the skin of a user prior to actuating the bandage 54 to close a wound.

With reference to FIGS. 7 and 8, the wound closing bandage 54 is again shown but now in a contracted position. The process as illustrated in these figures includes removing the adhesive covers 40 from the base ends, which includes the first end 28 of the female portion 20 and the second end 52 of the male portion 42. These base ends (28 & 52) may be placed on the skin of the user with the wound substantially in-line with the indicator line 30. The user may grasp the first end 50 of the male portion 42 and the second end 32 of the female portion 20, or the "pull ends" of the wound closing bandage 54. The user may place tension on the pull ends (50 & 32) to gently displace the first end 50 of the male portion 42 away from the second end 32 of the female portion 20. This movement may cause the locator tab 34 to be torn away from the male portion 42, or as shown here, the locator tab 34 may remain in contact with the male portion 42 and be torn away from the female portion 20. This may be the result of the tension applied by the user and the reduced section provided by the relief 36. Either way, the base ends, including the first end 28 of the female portion 20 and the second end 52 of the male portion 42 are drawn toward each other. With the base ends firmly adhered to the skin of a user, this would mean the skin on either side of the wound pad 48 would be drawn together, thus closing the wound.

Figure 10:
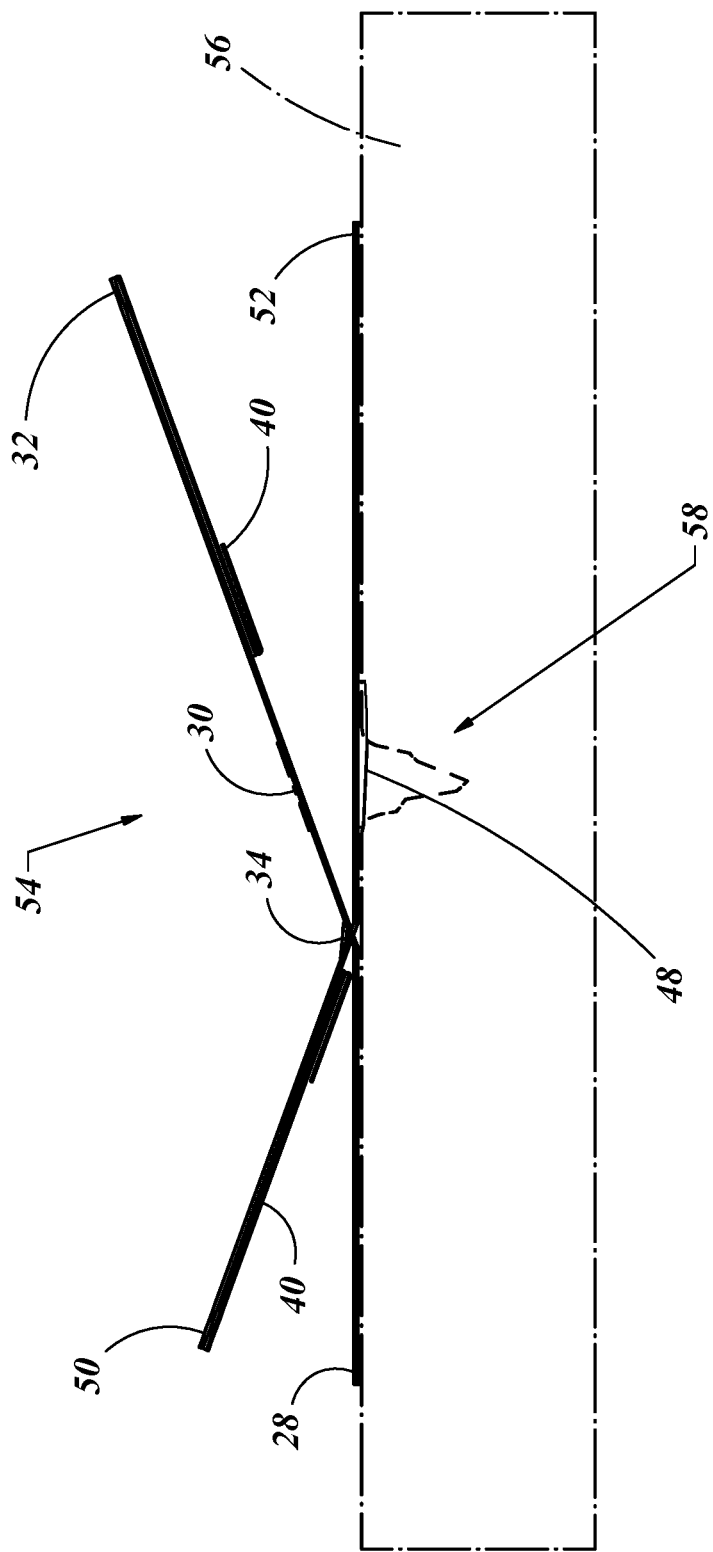
FIG. 10 is a side view of the wound closing bandage of FIG. 9, positioned over the open wound with the base ends of the male portion and the female portion adhered to the skin of a user.

The process of closing the wound with the wound closing bandage 54 is further illustrated in FIGS. 9-13. Referring to FIGS. 9 and 10, the wound closing bandage 54 is shown to be positioned on the skin 56 of the user with an open wound 58 located on the skin 56. The wound closing bandage 54 may be positioned with the indicator line 30 approximately over the center of the open wound 58. The base ends (52 & 28) may be placed on the surface of the skin 56, and adhered to the skin 56 by the adhesive patches 38. With the locator tab 34 still intact, proper location of the indicator line 30 will position the wound pad 48 over the open wound 58. The overall lengths of each of the male portion 42 and the female portion 20 may be a design solution that may vary for different wound criteria or other environmental factors. In general, the location of the adhesive patches 38 may be far enough away from the wound 58 to reduce the likelihood of any bodily fluids leaking from the open wound 58, or any cleansing or antibacterial dressings on the open wound 58, from interfering with the adhesive pads 38 in bonding to the skin of the user. The location of the adhesive pads 38 may also be close enough to the open wound 58 so as to generate sufficient surface tension in the skin to close the open wound 58 when tension is applied to the pull ends (30 & 50) of the wound closing bandage 54. This balance in the lengths of the female portion 20 and the male portion 42 of the wound closing bandage 54 is understood and is presented in what may be a typical relationship in the referenced figures of the present application.

Figure 11:
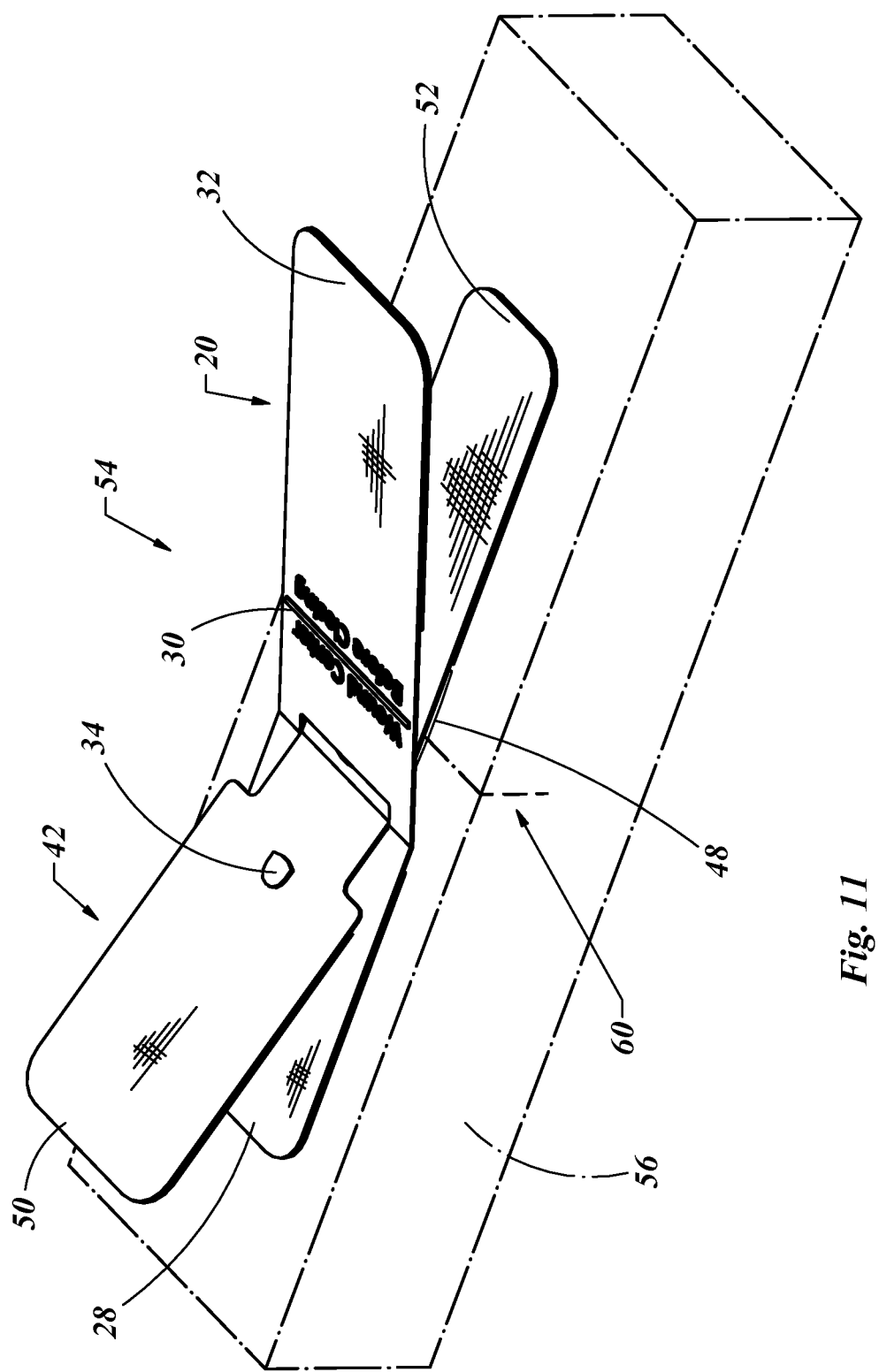
FIG. 11 is an isometric view of the wound closing bandage of FIG. 9 as it may be positioned over an open wound in the skin of a user, with the pull ends of the bandage being actuated thus contracting the base ends and closing the wound in the skin.
Figure 12:
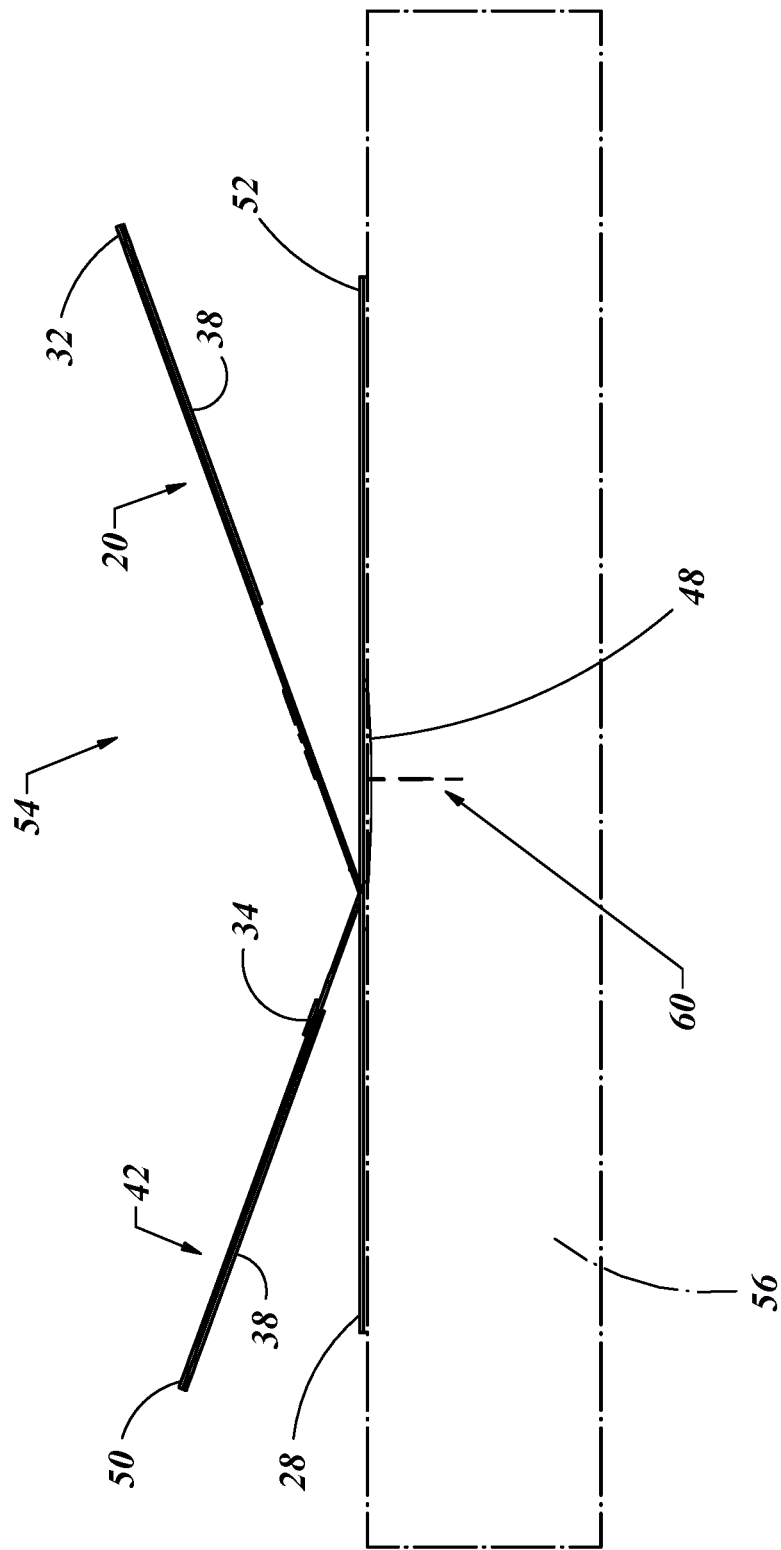
FIG. 12 is a side view of the wound closing bandage of FIG. 11, actuated such that the wound in the skin is closed.
Figure 13:
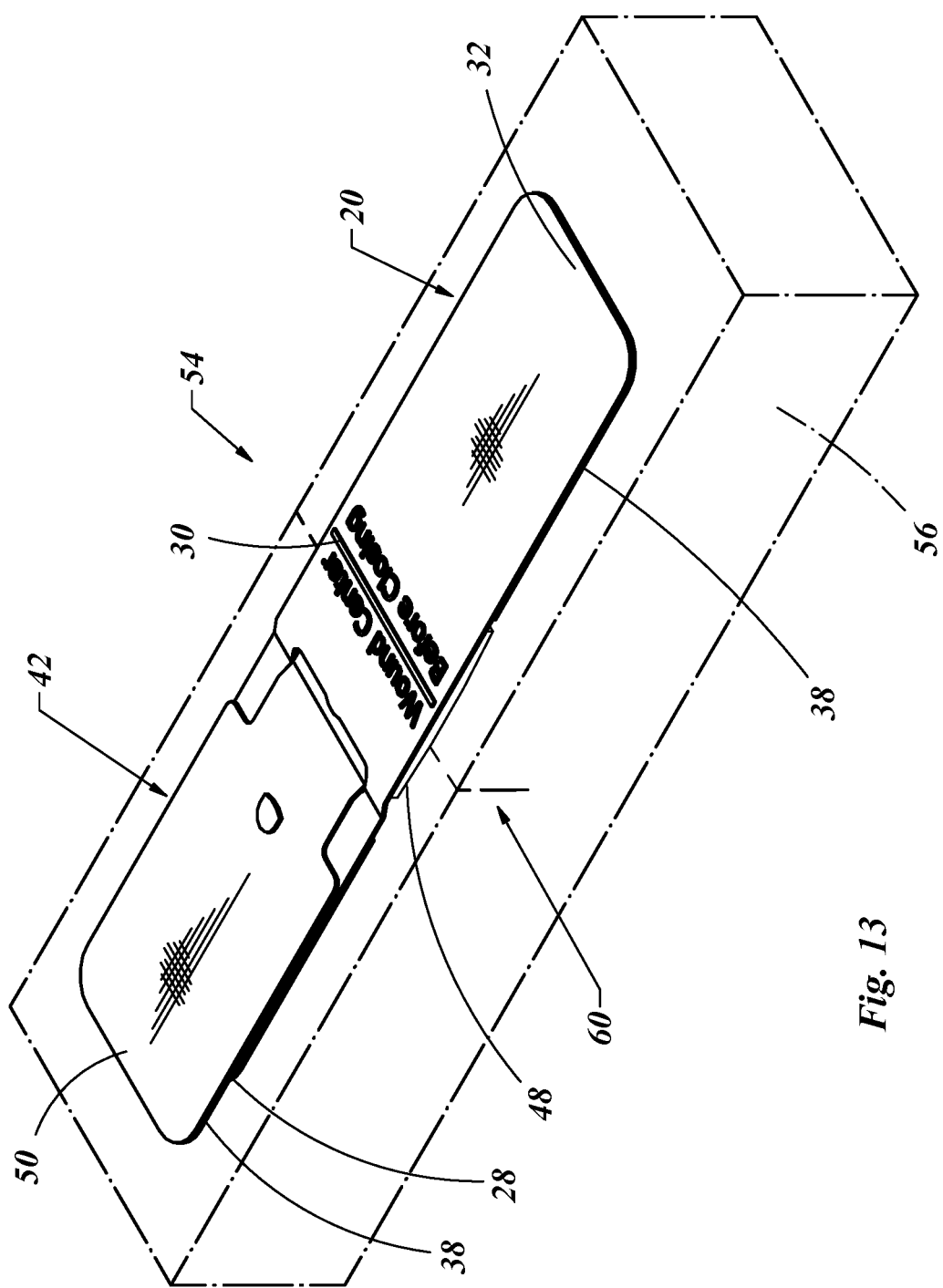
FIG. 13 is an isometric view of the wound closing bandage of FIG. 11 as actuated to close the wound and with the pull ends of the bandage secured to the base ends of the bandage and the skin, thus securing it in place.

To close the wound 58, the adhesive covers 40 may be removed from the second end 32 of the female portion 20 and the first end 28 of the male portion 42. Then, referring to FIGS. 11 and 12, the pull ends (32 & 50) may be grasped by the user and pulled away from one another. This action may result in applying a force to pull the surface of the skin 56 together, thereby closing the wound 60. The process of pulling the second end 32 of the female portion 20 away from the first end 50 of the male portion 42 may result in detachment of the locator tab 34 from the female portion 20, as is depicted in FIGS. 11-13. As previously mentioned, the locator tab 34 may detach from the male portion 42, thus maintaining the integrity of the locator tab 34 with the female portion 20. An intended use of the locator tab 34 may be to position the female portion 20 in a consistent orientation relative to the male portion 42 when the wound closing bandage 54 is first placed on the skin 56, thus providing consistent orientation of the wound pad 48 relative to the open wound 58.

The adhesive patches 38 at the second end 32 of the female portion 20 and the first end 50 of the male portion 42 may be exposed. Referring to FIG. 13, the second end 32 of the female portion 20 and the first end 50 of the male portion 42 (pull ends) of the wound closing bandage 54 may be secured down onto the second end 52 of the male portion 42 and the first end 28 of the female portion 20 (base ends) respectively, and also any exposed skin 56 not covered by the base ends (28 & 52). Tension may be maintained on the second end 32 of the female portion 20 and the first end 50 of the male portion 42 as these pull ends (32 & 50) of the wound closing bandage 54 are secured to the skin 56 by way of the adhesive patches 38. By maintaining tension on the pull ends (32 & 50), tension is transferred to the skin 56 to transform the open wound 58 (FIG. 9) to the closed wound 60 shown here. The indicator line 30 may no longer coincide with the location of the closed wound 60. This may not be relevant in that what may be important is for the wound pad 48 to be over the surface of the closed wound 60, after the wound closing bandage 54 has been actuated, as shown in FIG. 13. The location of the indicator line 30 may be positioned on the female portion 20 to take into account the movement of the wound pad 48 on the male portion 42 relative to the wound as the wound closing bandage 54 is actuated into this closed wound position.

The result of this process may be providing and maintaining tension in the skin by pulling one end of the open wound 58 toward the other end of the open wound 58, thereby closing the wound 60. Placing the tissue of the skin together in this manner allows the skin to heal properly, minimizing the extent of the scaring. Traditional sutures, which cut through the layers of the skin, have a single positive purpose, also to close the wound. The wound closing bandage 54 does so without the necessity of puncturing the skin multiple times to place the sutures in the skin. As such, the wound closing bandage 54 may be used by people without medical training. This may be necessary for those injured where medical help is not immediately available. This may be used in a high level emergency such as in a military combat zone or as common as a hiker tripping over a rock while on a remote trail. The absence of the need to puncture the skin for sutures may also eliminate the need for any local analgesic or anesthetic, which is typically used to numb the skin so sutures can be added without additional pain to the patient.

The timing of suture removal is also a bit art and science. If the sutures are removed too soon, the wound can open up as the outer layers of the skin are not yet healed together. If the wound opens, the likelihood of more extensive scarring is increased. If the sutures are left in too long, the skin will begin to scar around the sutures as well as the previously open wound. This results in what is referred to as "railroad tracks" commonly seen as a series of dots on either side of the original wound. The wound closing bandage 54 in all forms eliminates the need for sutures and therefore each of these limitations. If the wound closing bandage 54 is removed too early or comes off inadvertently, a replacement wound closing bandage 54 may be applied immediately without the need for medications, or a person with medical training. Also, the wound closing bandages 54 may be left on for an extended period as there are no complications such as increased scarring and skin irritation which could be caused by having a foreign body in the form of a nylon thread, in the skin.

Figure 14:
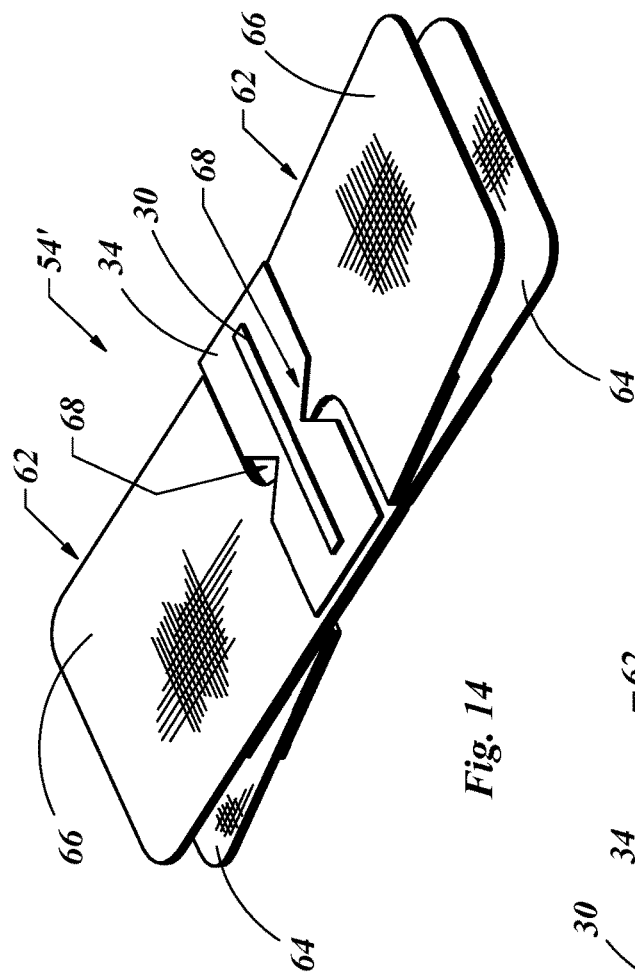
FIG. 14 is an isometric assembled view of a preferred embodiment of a wound closing bandage of the present invention.
Figure 15:
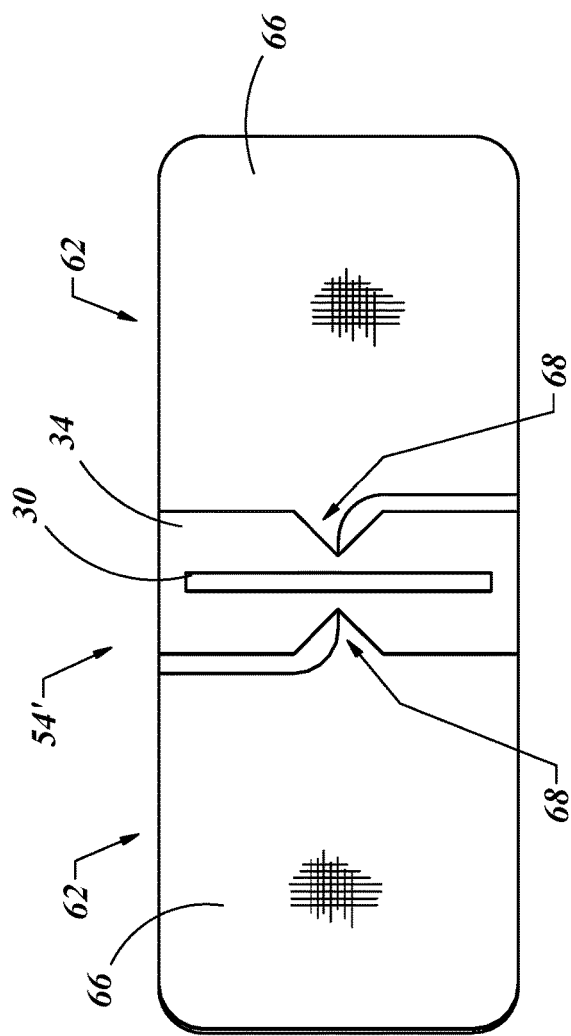
FIG. 15 is a plan view of the wound closing bandage of FIG. 14.

An alternative preferred embodiment of the present invention is shown in FIGS. 14-25. With reference to FIGS. 14-15 a wound closing bandage 54' is shown in an assembled state. The wound closing bandage 54' may be comprised of two U-shaped members 62 interwoven such that a first end 64 is present on a lower side of each end of the wound closing bandage 54'. A second end 66 of each of the U-shaped members 62 may then be positioned above the first ends 64. The far edges of the first end 64 and the second end 66 on each end of the wound closing bandage 54' may be positioned such that they aligned with one another in the starting position. Each of the U-shaped members 62 may be held in this position by the locator tab 34. The locator tab 34 may include an indicator line 30, which may provide alignment assistance to the user such that the indicator line 30 may be positioned over the center of the wound or incision of the user. The locator tab 34 may include a relief 68, which may provide an intentional stress point where the locator tab may separate upon application of a shear force to the applicator tab 34.

With reference to FIG. 16, a bottom view of the wound closing bandage 54' is shown. The first adhesive covers 70 are shown as they may be covering the bottom of the first ends of each U-shaped member 62. The first adhesive cover 70 may include a first tab portion 72, which may be raised above the surface of the rest of the first tab portion 72 to facilitate grasping the tab to remove it by a user. The first adhesive cover 70 may be used to protect and maintain the tactile properties of the adhesive presented underneath the first adhesive covers 70, and therefore the bottom portion of each U-shaped member 62. The adhesive may be present on the entire bottom side of each U-shaped member 62 and not use a wound pad 48 as shown in previous embodiments.

With reference to FIG. 17, the wound closing bandage 54' is shown in a partially disassembled state to more clearly show the two U-shaped members 62 being separated from one another and their locations relative to the locator tab 34. As can more clearly be seen in this view, the U-shaped members 62 may include a reduced section 74 created by a removal of some of the material to form the U-shaped members 62. In this embodiment, the reduced section 74 may be located near the center along a long axis of each U-shaped member 62. The reduced section 74 of each U-shaped member 62 may allow each of the two U-shaped members 62 to be interlaced such that the reduced section 74 areas are placed adjacent to one another. In this embodiment, the reduced section 74 may be approximately ½ of the width of the widest portion of the U-shaped member 62. Thereby, when assembled as previously shown, the wound closing bandage 54' may have the total width of that of the widest portion of one of the U-shaped members 62. The resultant may be that there is some overlap in a portion of each of the U-shaped members 62 relative to the other U-shaped member 62 when positioned in this manner. This overlap may not be 50% of each of the U-shaped members 62 as shown and described above, but a portion of each of the U-shaped members may overlap in this manner. The value of this design will become more evident later in this disclosure.

Figure 18:
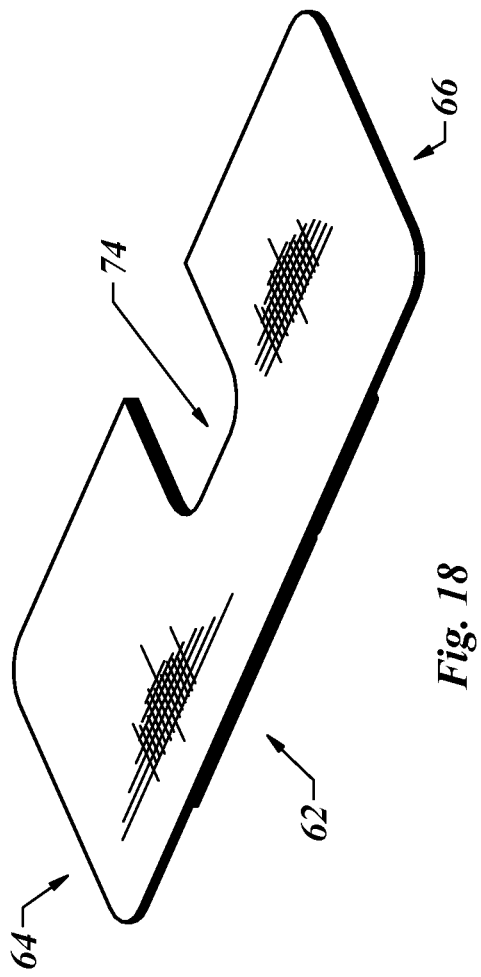
FIG. 18 is a top isometric view of one of the U-shaped sections of the wound closing bandage of FIG. 14.
Figure 19:
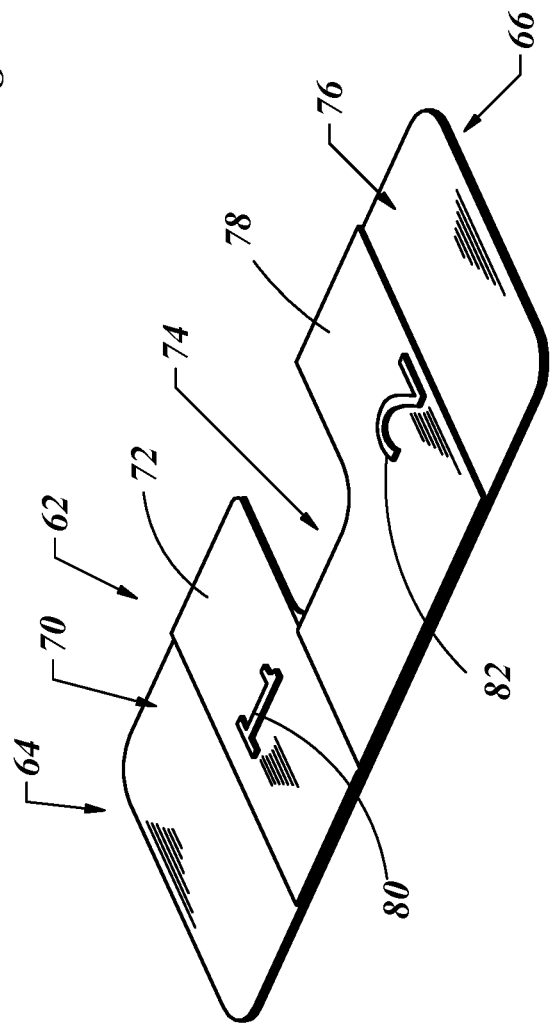
FIG. 19 is a bottom isometric view of one of the U-shaped sections of the wound closing bandage of FIG. 14.

With reference to FIGS. 18-19 a single U-shaped member 62 is shown from a top view in FIG. 18 and a bottom view in FIG. 19. Each U-shaped member 62 may include a first end 64 and a second end 66. From the top view, the first end 64 may be indistinguishable from the second end 66 in that the reduced section 74 may be provided in the center with respect to the long dimension of the U-shaped member 62. In the bottom view, a distinction between the first end 64 and the second end 66 may be provided in that the first adhesive cover 70 may cover the adhesive backing of the U-shaped member 62 from the first end 64 to the closer edge of the reduced section 74. A second adhesive cover 76 may be provided on the second end of the U-shaped member 62 and extending all the way to its far edge of the reduced section 74. The second adhesive cover 76 may include a second tab portion 78. The second tab portion 78 may provide similar assistance in removing the second adhesive cover 76 as the first tab portion 72 offered to the removal of the first adhesive cover 70. The first tab portion 72 and the second tab portion 78 may be marked with the numerical number one 80 and a numerical number two 82, respectively. This may be of assistance in the instructions to a user, as the user may be under stress due to some accident or injury to themselves or another person to which they are offering assistance. As noted, each tab portion (72 & 78) may include a free end which may allow a user simple access to grab and pull to remove each adhesive cover (70 & 76), thereby making the adhesive underside of the material of the U-shaped member 62 accessible.

The "U shape" of the U-shaped member 62 may be desirable in that the goal is to place the first end 64 on the skin, it being held in place by the adhesive on the bottom side of the first end 64 after removal of the first adhesive cover 70. In pulling on the second end 66 it may be desirable to pull relatively evenly across the entire width of the first end 64 of the U-shaped member 62. Due to the overlap of a portion of each U-shaped member 62 relative to the adjacent U-shaped member 62, a more even force may be applied to one side of the wound and also to the other side of the wound by the first ends 64 of the second U-shaped members 62. This overlap may provide less twisting of the edge of the wound as the wound is pulled together and into a closed position. The "U shape" of the U-shaped member 62 may allow tension to be generated across the entire width of the U-shaped member 62, which is then transferred to the skin to which the first end 64 of the U-shaped member 62 is adhered. By doing this on either side simultaneously, this may close the wound more evenly with less twist or shear on the wound as opposed to two straight strips running adjacent to one another and without any overlap, in which the force application in each direction toward the center line is now offset by the width and placement of each of the parallel strips. The interlocking of the two U-shaped members 62 by way of the reduced section 74, may cause a complete overlap so that the tension is applied substantially linearly across the center of each of the U-shaped members 62, thus providing a substantially even compressive force on the wound to close the wound evenly.

Figure 20:
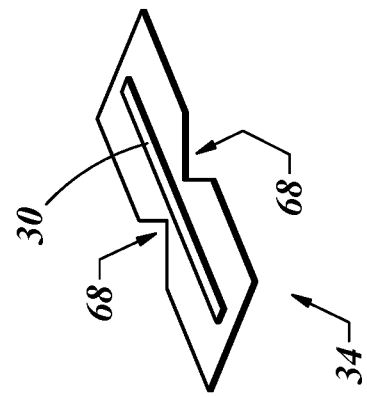
FIG. 20 is a top isometric view of the locator tab of the wound closing bandage of FIG. 14.

The locator tab 34 is shown in FIG. 20 as it may be used in this embodiment. The locator tab 34 may include an indicator line 30. Indicator line 30 may be silkscreened or printed on the top of the locator tab 34. The locator tab 34 may also include a relief 68, which may be comprised of a reduced area of material of the locator tab 34, so as to allow the locator tab 34 to split one side from the other at the location of the relief 68. The purpose of the locator tab 34 may be to provide a conditionally secure orientation of each of the two U-shaped members 62, relative to one another. When the wound closing bandage 54' is applied to the skin and used, the locator tab 34 may be split, in that the orientation of the U-shaped members 62 relative to one another will change during the application of the wound closing bandage 54'. This will become apparently clear in the figures to follow. It is shown here that the locator tab 34 may be comprised of a separate piece of material which may include an adhesive backing, as may be adhered to each of the two U-shaped members 62. An alternative may be to provide a printed indicator line 30 directly on each U-shaped member 62 and then separately provide a locator tab that would secure the U-shaped members 62 relative to one another in the appropriate starting position.

As noted above, in this embodiment the wound pad 48, as shown in FIG. 13, has been omitted in the embodiment as shown in FIGS. 14-31. In some cases it may be desirable to provide adhesive contact close to the edges of the wound or incision at the surface of the skin. When the adhesive material is also present in the area comprising the reduced section 74, these areas of the wound closing bandage 54' may help to secure the skin to prevent sheering movement of each side of the wound or incision of the skin during healing. The direction of sheer may be defined as movement of the skin on one side of the incision or wound relative to the position or movement of the skin on the other side of the wound or incision along the length of the wound or incision. If contact is only made on each side of the incision and connections are made between the opposing sides without touching or securing the skin between the portions mounted to the skin, there may be a reduced restriction to these sheer forces generated during normal movement. If the healing skin breaks free, either by being pulled apart or by sheer, there may be additional scar tissue that is generated due to a repeated cycle of partial healing, damage and then healing again. This sheer stress may be reduced by bonding the center portions of the wound closing bandage 54' directly to the skin immediately adjacent to the wound, now closed by the application of the wound closing bandage. This is further illustrated in the following FIGS. 21-24.

Figure 21:
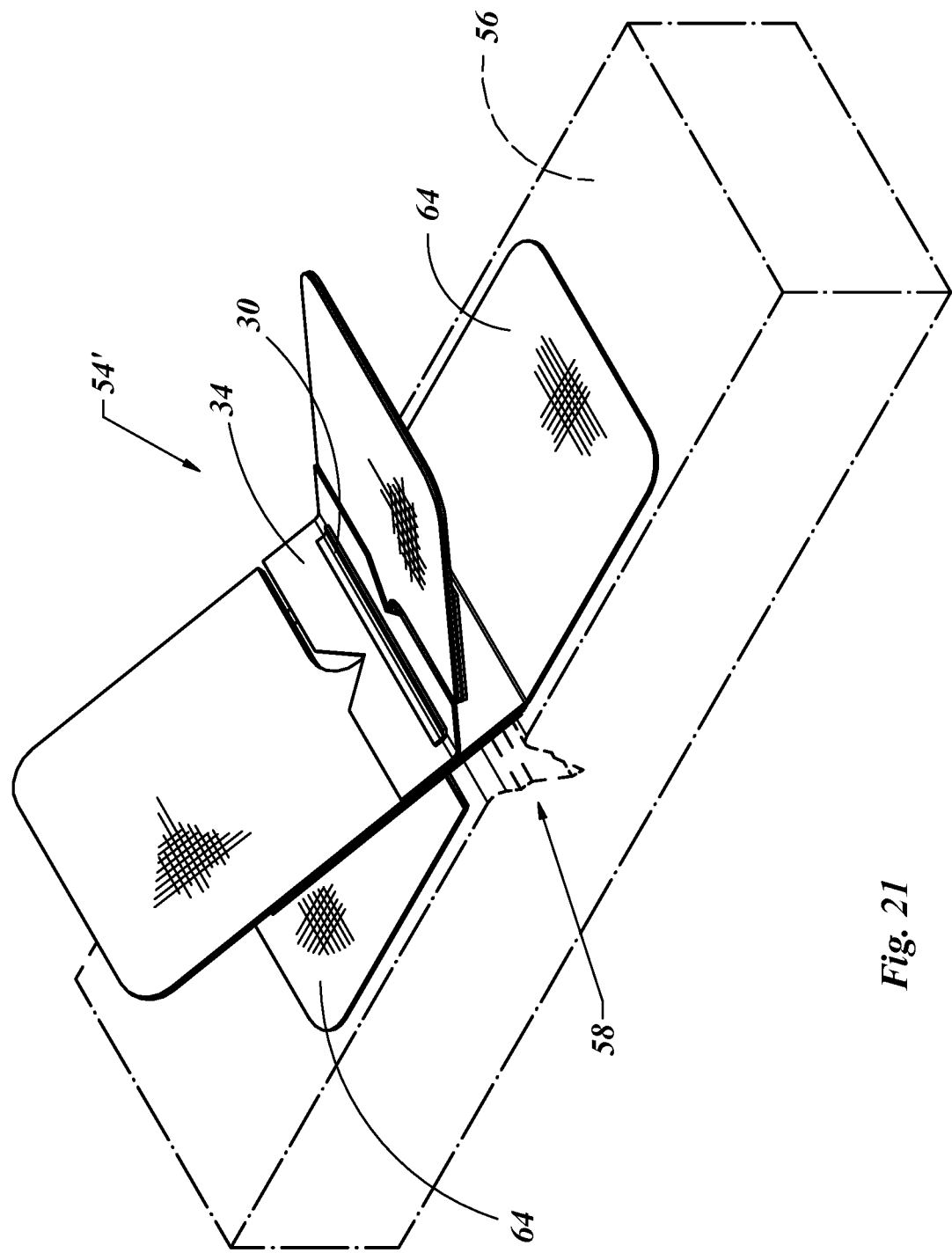
FIG. 21 is an isometric view of the wound closing bandage of FIG. 14 shown in use is applied to an open wound.
Figure 22:
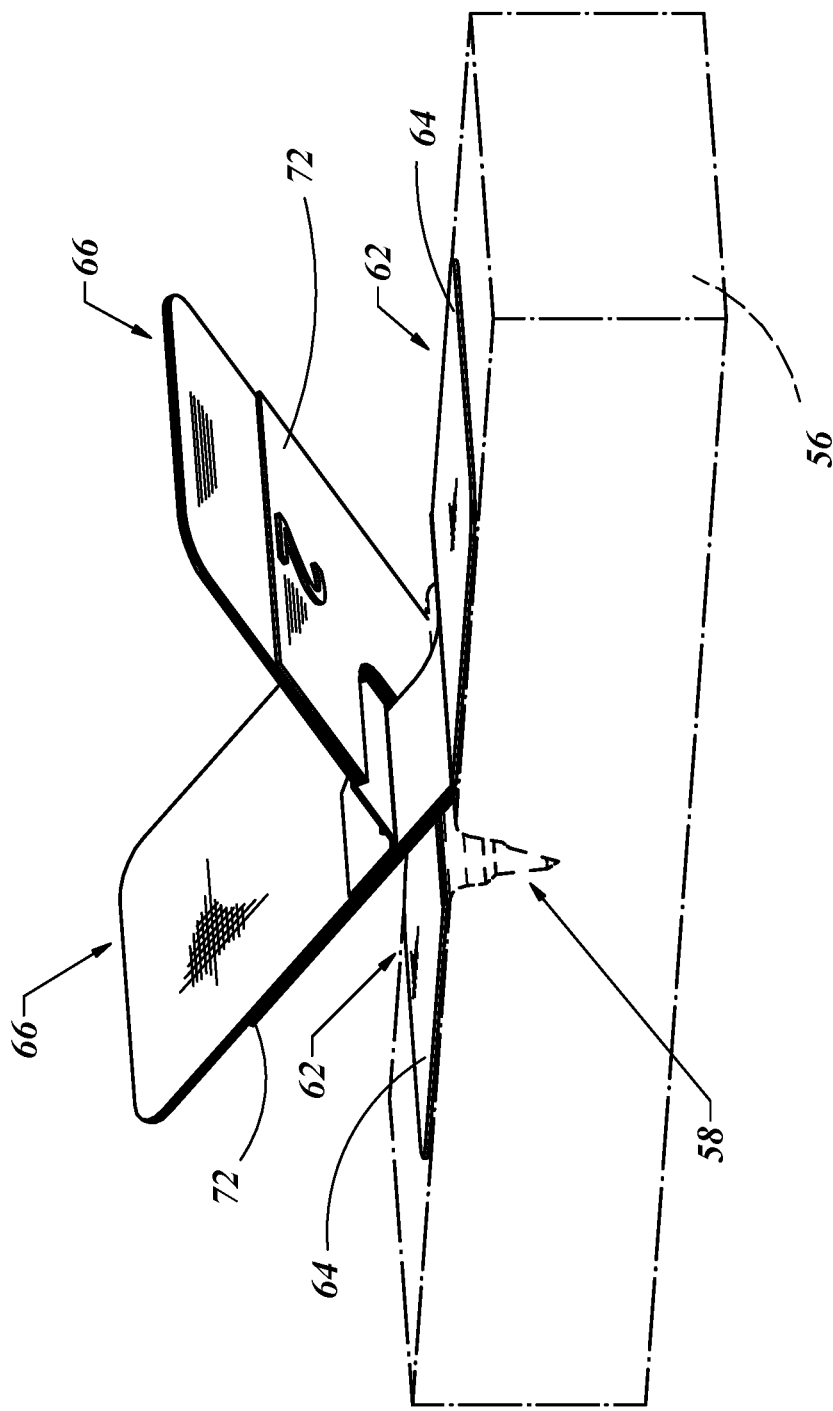
FIG. 22 is an isometric view of the wound closing bandage as shown in FIG. 21, further showing the underside of the second end of the wound closing bandage of FIG. 14

With regard to the use of the wound closing bandage 54', a sequential illustrated example of use of this embodiment is shown in FIGS. 21-24. In FIGS. 21-22 a wound closing bandage 54' is shown as it may be placed on the skin 56 of a user, which includes an open wound 58. The first ends 64 may be adhered to the skin 56 of the user by previously removing the first adhesive covers 70 on each of the first ends 64 of each U-shaped member 62 and securing the first ends 64 to the skin 56 on each side of the open wound 58. As is shown, the second ends 66 of each of the U-shaped members 62 are not adhered to the skin 56 at this point. The indicator line 30 of the locator tab 34 is shown to be proximate to, but elevated above, the open wound 58. The first ends 64 of each of the U-shaped members 62 of the wound closing bandage 54' may be secured to the skin 56 and the second adhesive covers 72 of the second ends 66 of each U-shaped member 62 may be removed, exposing the adhesive on the bottom of the second ends 66.

Figure 23:
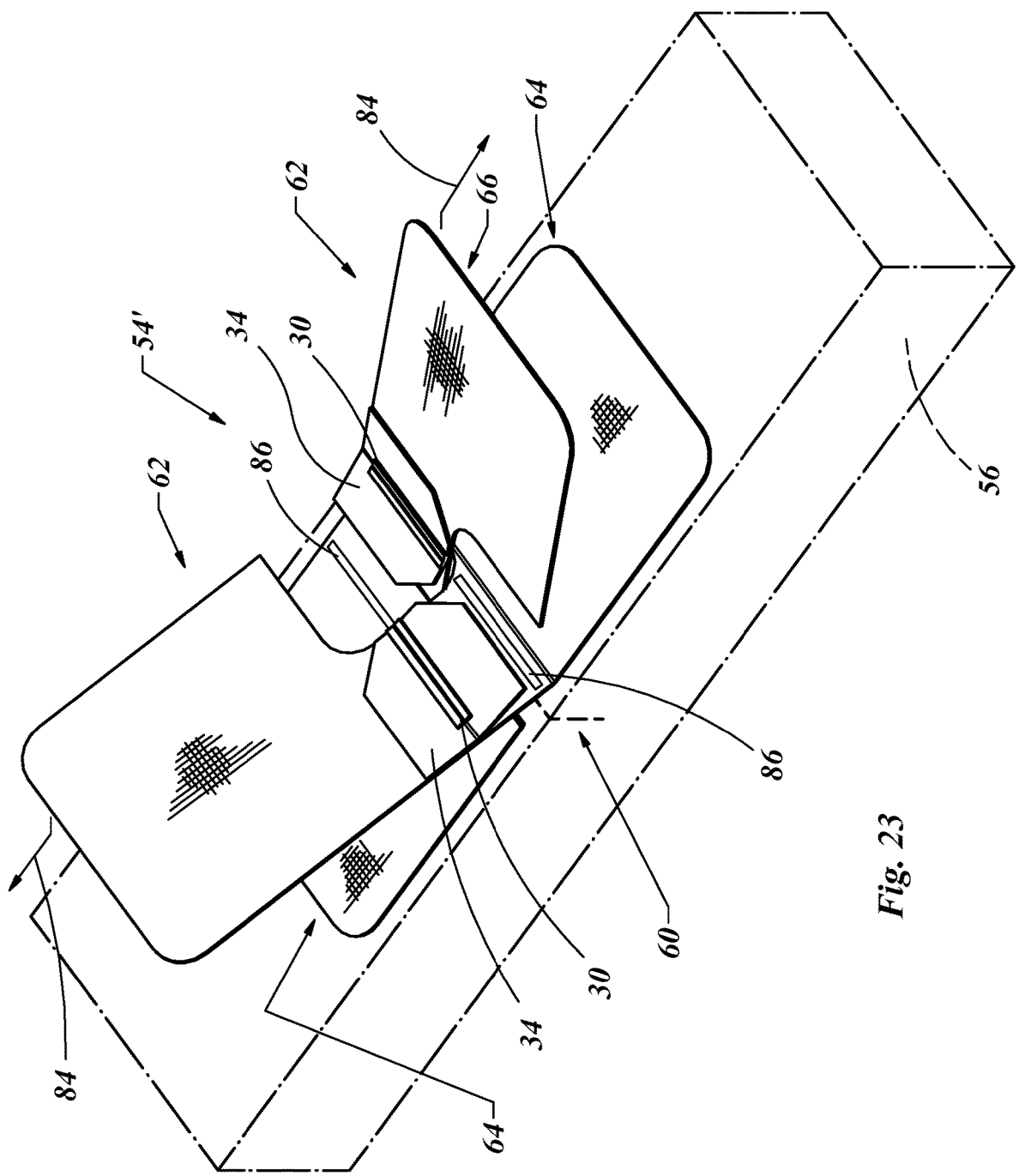
FIG. 23 is an isometric view of the wound closing bandage of FIG. 14 in use such that the wound is closed, also showing the tension indicator line.
Figure 24:
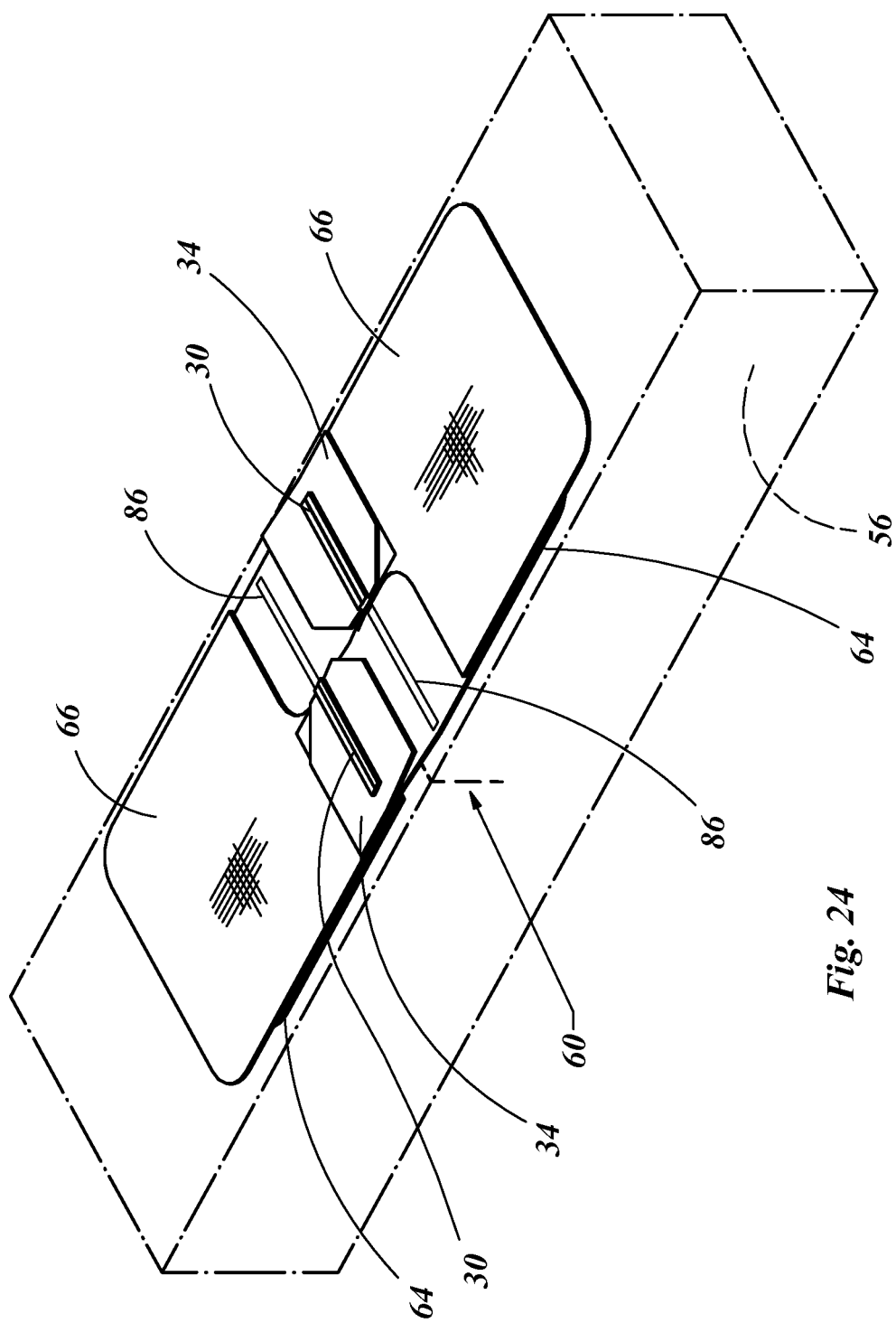
FIG. 24 is an isometric view of the wound closing bandage of FIG. 23, wherein the wound is closed and the bandage secured to the skin and showing the tension indicator lines.

With reference to FIGS. 23-24, the second ends 66 of each U-shaped member 62 may be pulled away from each other, as illustrated by the arrows 84. This action may cause the locator tab 34 to split, with each half maintaining its orientation with each of the two U-shaped members 62. At this point it is clear that the indicator line 30 may be split by the force applied to pull each of the U-shaped members 62 away from one another and overcome the integrity of the locator tab 34. It may split, as shown here, or be torn away from one or both of the U-shaped members 62. If the locator tab 34 is split, there may now be two shortened indicator lines 30, which may no longer be collinear. A tension indicator line 86 may be provided on each U-shaped member 62 so as to provide a reference where each of the now two indicator lines 30 may align to give the user a relative guide as to how much force is needed to apply to each of the second ends 66 of each of the U-shaped members 62 to adequately turn the previously open wound 58 into a closed wound 60. The second ends 66 of the U-shaped members 62 of the wound closing bandage 54' may then be secured down to the skin 56 and/or top surface of the first ends 64 of the U-shaped members 62 positioned directly under each of the respective second ends 66. This is illustrated in FIG. 24. Here it can also be seen how each portion of the now two shorter indicator lines 30 may be in alignment with their respective tension indicator lines 86.

The desired material which comprises each U-shaped member 62 may be an engineering choice, but the applicant has found certain advantages to providing a material with certain elastic properties. As previously discussed, and further illustrated in the figures, the purpose of the wound closing bandage 54' is to secure the first end 64 of each U-shaped member 62 to the skin of the user on each side of an open wound or incision. The second ends 66 of each U-shaped member are then pulled apart from one another and then secured to the skin 56 or the top of the first end 64 of the U-shaped member located underneath that second end 66. This pulling process pulls the open wound 58 to a closed wound 60 where it can be maintained in that closed position to facilitate healing of the wound or incision.

In order to maintain the wound closing bandage 54' on the skin of the user it has been found that an elastomeric bandage material within a set range of elastic properties may be desirable. The elastic properties may coincide with elastic properties of the skin. Human skin has a modulus of elasticity (Young's modulus) of approximately 2 MPa (mega-Pascals). The thickness of human skin varies from 0.2 mm of the human eyelid to as high as 6.0 mm on the sole of the foot. On average, though it may vary with the age and sex of the individual, a reasonable average skin thickness on the extremity or torso of an individual is approximately 3.0 mm thick. Therefore, if we look to provide a material with a similar spring constant compared to that of the skin with that thickness, that material may be similar to the 2 MPa value multiplied by the inverse of the thickness of the material (mm) times the thickness of the skin, or approximately 3 mm. Therefore, if a material used for the wound closing bandage 54' is 1 mm thick, a modulus of elasticity of the material which would coincide with the elastic properties of that of human skin may be approximately 6 MPa. In that the goal of the wound closing bandage 54' is to create a temporary artificial skin to substitute for a loss of integrity of the skin caused by the incision or wound, it may be desirable that the structural integrity of the material of the wound closing bandage 54' be similar to that of the skin, as it is in essence, replacing those properties of the skin on a temporary basis.

As an incision or cut is an injury to the skin 56, we would imagine the user would be somewhat protective of that area until it heals and therefore would be careful so as to not place excessive stress on the wound/incision site that would normally take the skin 56 to a failure point. As such, a proposed value of a desirable material with the aforementioned thickness of 1 mm could have a modulus of elasticity that is less than that of the skin 56, or factoring in the reduced thickness of the bandage relative to the skin, the 1mm thick bandage could have a modulus of elasticity of less than 6 MPa. The applicant has experimented with different materials and found good results with a 1 mm thick material with a modulus of elasticity of approximately 0.40 MPa. It is therefore suggested for a 1 mm thick U-shaped member 62 of the wound closing bandage 54' (or any other embodiment) that a material may function optimally with an equivalent modulus of elasticity (some composite and woven materials are not homogenous and therefore not traditionally identified by the modulus of elasticity, so an equivalency may be used to provide similar material properties of the material combination) of between 0.30-6.0 MPa.

The amount of tension applied to each of the two second ends 66 of the wound closing bandage 54' to close a 1 inch (25 mm) long incision may be in the range of 1.5-30.0 Newtons (5.4-108.0 oz (6.75 lbs)). At a specific thickness of the wound closing bandage 54' for each inch of width of the wound closing bandage, the force (F) required to apply tension to the two second ends may comply with the following equation:

$$F = Y * S * (\Delta L/L)$$

where S is the cross sectional area of the section of the wound closing bandage 54', Y is the Modulus of Elasticity of the material and ΔL/L is the relative change in length of the material when tension is applied to the wound closing bandage 54' to close the wound. If a 1 mm thick by 25.4 mm wide wound closing bandage 54' is used and stretched by 20% of the resting length upon application to close the wound, a material with a "Y" of 0.3-6.0 MPa would yield 1.5-30.0 N of force. This force (F) may be generally provided as tension to close the wound. This tension may be desired to be maintained for a minimum of seventy-two hours, at which time the wound is usually considered "waterproof". This means the healing process may be sufficient to allow for normal bathing of the skin with minimal if any disruption of the healing process. In most cases it may be desirable to continue with the compressive force to join the edges of the wound or incision together and also provide a restriction against sheer forces for up to fourteen days after the injury or surgery. This suggests that the material of the wound closing bandage 54, in any embodiment as disclosed, would provide a spring constant so as to allow this tension to be provided below any sort of yield limit of the material, or material combination, in that the material would be able to maintain this tension for a number of days even after additional stresses may be applied to the material of the wound closing bandage 54 from movement of the skin 56 to which the wound closing bandage 54 is applied. This additional stress may result from any movement or activity of the user.

The elastic properties of the material may allow for this aforementioned movement of the skin 56 resulting from activity of the user, with the wound closing bandage 54 maintaining its position on the skin, so as to minimize the likelihood of tearing the bandage 54 free from contact with the skin 56 while maintaining tension to close the wound and keep it stable. If a rigid element is adhered to the skin 56, which has a much higher modulus of elasticity as compared to the skin 56, also obviously depended on the thickness of the material, that rigid element will fight any movement of the skin 56 when the body moves, as the skin 56 may naturally flex much more than the rigid material with a high modulus of elasticity. If the securing structure made of this rigid material does not flex with the skin 56, the skin 56 may begin to tear loose from the rigid element attached to the skin 56. This may cause abrasions and irritation to the surface of the skin 56 which may be very uncomfortable to the user. If the rigid element tears loose from the skin 56, the rigid element may lose its ability to function in that adequate force may no longer be applied to keep the wound closed so it can properly heal.

As an example, plastics such as polypropylene have a modulus of elasticity of up to 2 GPa (2,000 MPa). Nylon has a modulus of elasticity of up to 4 GPa (4,000 MPa). When nylon is used as a suture, the amount of skin 56 the nylon suture is anchored into on each side of the previously open wound or incision is only a couple millimeters. Therefore, the amount of movement necessary in that small area of skin 56 can easily be transferred to the adjacent skin fibers, thus maintaining a very rigid connection between each side of the previously open wound or incision with a minimal chance of tearing under normal circumstances. With that said, it has been found that the wound closing bandage 54 in various forms of the disclosed invention provides much less physical discomfort to the user throughout the healing process as compared to traditional nylon sutures. The wound closing bandage 54 of the present invention also results in less scarring and has a similar healing time when directly compared to traditional nylon sutures.

When a larger rigid structure with a modulus of elasticity of 1000-2000 times that of the skin 56 is applied to the surface of the skin 56, the ability for the skin 56 to move and flex, as this would under normal activity, may be compromised. If the structural element loses its bond with the surface of the skin, because the skin 56 is moving relative to the structural element, the adhesive bonding the structure to the skin 56 may fail or tear the skin 56. When this happens, as previously noted, the structural element no longer functions to hold the skin 56 on one side of the incision or wound in a stable position relative to the other side of the incision or wound. If this happens the rigid device no longer functions in its intended purpose. A rigid element secured to the surface of the skin 56 on each side of the wound may be adequate with a substantially immobile patient, but may be problematic in conditions where the user is physically active soon following the wound closure process.

A more flexible material may solve this problem in that the adhesive may be less aggressive in that the more pliable material will move with the skin 56, while providing suitable structural integrity over the skin 56 separated by the wound or incision. This may help to maintain a relatively stable environment for the closed wound 60 or incision, preventing the wound from opening again or sheering. This has been found to facilitate proper healing of the wound while minimizing scaring and discomfort to the user.

Figure 25:
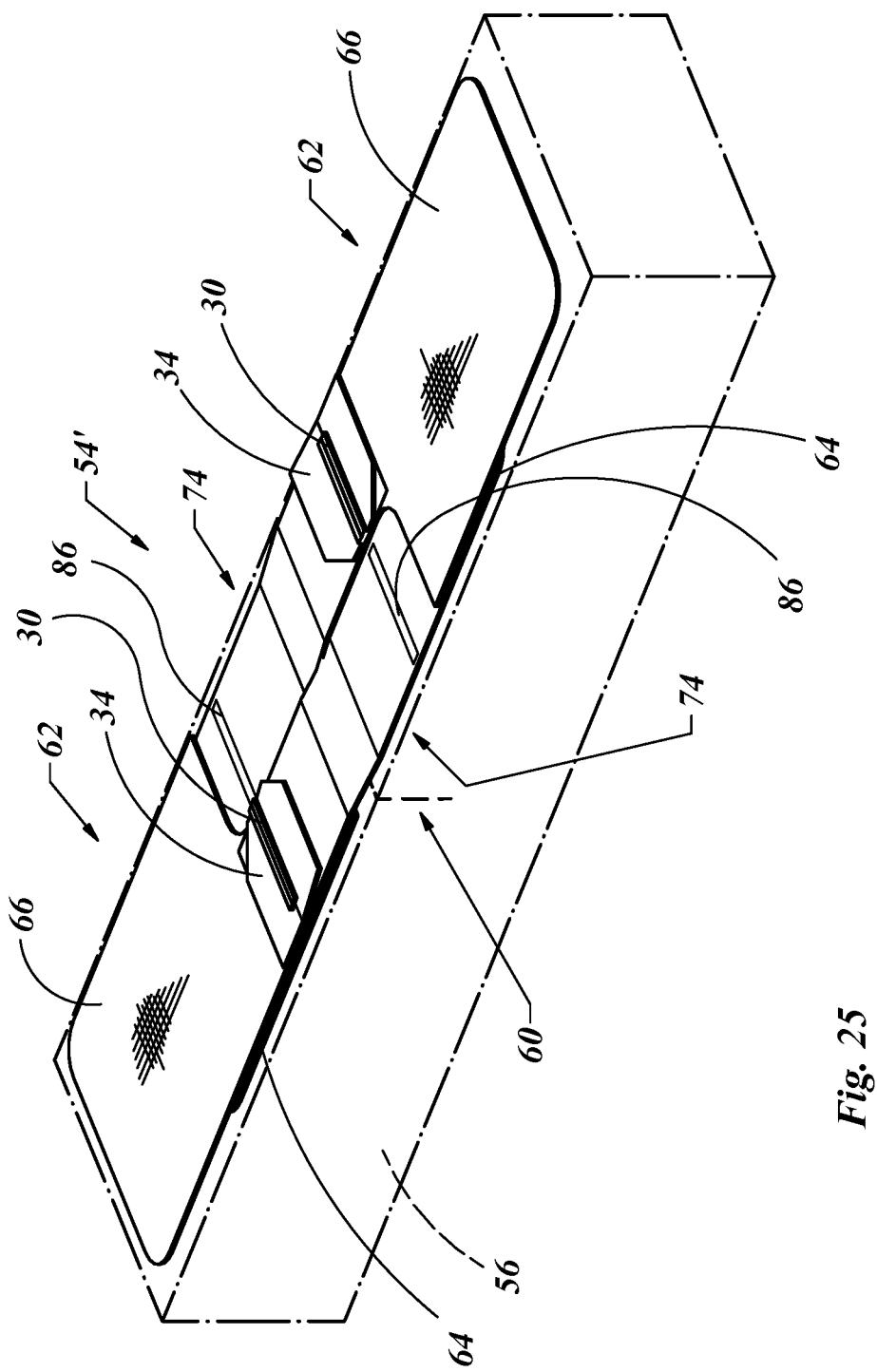
FIG. 25 is an isometric view of the wound closing bandage of FIG. 24, wherein the wound closing bandage is in a stretched state, also showing the tension indicator lines

The use of a wound closing bandage 54' with more apparent elastic properties is illustrated in FIG. 25. The reduced section area 74 may be most likely to stretch, due to the reduced section of what may be a homogenous material or material composite, including a woven material with an adhesive backing which may comprise each of the U-shaped members 62. As noted, a suggested tension to close a 1 inch wide wound 60 may be 1.5N to 30.0N applied to each of the second ends 66 of the U-shaped members 62 of the wound closing bandage 54'. Upon applying tension to the second ends 66, the locator tab 34 may break free, thereby allowing movement of the second ends 66 relative to one another. A tension indicator line 86 may be provided on each U-shaped member 62 so that when a predetermined amount of tension, and therefore stretch, in the U-shaped members 62 is provided, the indicator line 30 on the locator tab 34 may align with the tension indicator line 86 on the other U-shaped member 62. This may signal the person applying the wound closing bandage 54' that sufficient tension has been achieved and then secure the second ends 66 to the skin 56 and/or the top of the first ends 64 under the respective second ends 66. In that the material which constitutes each of the U-shaped members 62 has elastic properties, this figure shows how the second ends 66 may extend beyond most or all of the first ends 64 already bonded to the skin 56. The physical stretching of the material of the U-shaped members 62 may allow for a significant amount of movement of the skin, and therefore the wound closing bandage 54' while still maintaining tension to keep the wound 60 securely closed. A very rigid material may not allow for compliance with this movement of the skin 56.

A woven elastic material or similar material may also be preferred in that this material may allow the wound 60 to "breathe". This means moisture may be evaporated from the skin surface by being allowed to pass through the semipermeable material of any embodiment of the wound closing bandage 54. In this disclosure, the term "semipermeable" may be used to describe a material that may allow for moisture to pass through the material. This may allow the wound closing bandage 54' to completely cover the wound 60 without preventing moisture from evaporating from the surface of the skin covered by the wound closing bandage 54'. A rigid material such as many plastics, are typically impervious to water and therefore if left in direct contact with the skin 56, may result in a reduced rate of healing of the wound 60, greater irritation of the skin 56 and even a degradation of the integrity and health of the skin 56.

Another embodiment of the wound closing bandage 54" of the present invention is shown in FIGS. 26-31. With reference to FIGS. 26-28, an alternative to the U-shaped member 62 is presented as an I-shaped member 88. The difference is instead of a single reduced section 74 of the U-shaped member 62 being on one side and substantially equal in depth to one-half of the total width of the U-shaped member 62, the I-shaped member 88 has two reduced sections 90, one on each side of the I-shaped member 88. The reduced sections 90 of each I-shaped member 88 may be substantially centered with respect to a first end 92 and a second end 94. The bottom portion of each I-shaped member 88 may also include a first adhesive cover 70' with a first tab portion 72' and a numerical number one 80' to cover the adhesive backing on the first end 92. Likewise, covering the adhesive backing of the second end 94 may be a second adhesive cover 76' with a second tab portion 78' and a numerical number two 82'. The function and assembly of this embodiment of the wound closing bandage 54" may be similar to that as previously shown and described with the wound closing bandage 54' using two U-shaped members 62, including the location of the I-shaped members 88 relative to one another by way of a locator tab 34, which may include an indicator line 30.

The difference with the I-shaped members 88 is that these members have a center section 94 which may connect the first end 92 to the second end 94 which may be centered with respect to the overall shape of the I-shaped member 88, as opposed to the eccentric shape of the U-shaped member 62 as shown previously. The first end 92 of one I-shaped member 88 may be partially overlapped by the second end 94 of the other I-shaped member 88 of the wound closing bandage 54". This overlap, though not as complete of an overlap as using the U-shaped members 62, may provide a distribution of load to the skin to pull the edges of the open wound 58 to a closed wound 60 with a reduced amount twisting of the skin 56 as opposed to two parallel strips with no overlap or even a gap between the strips.

Figure 29:
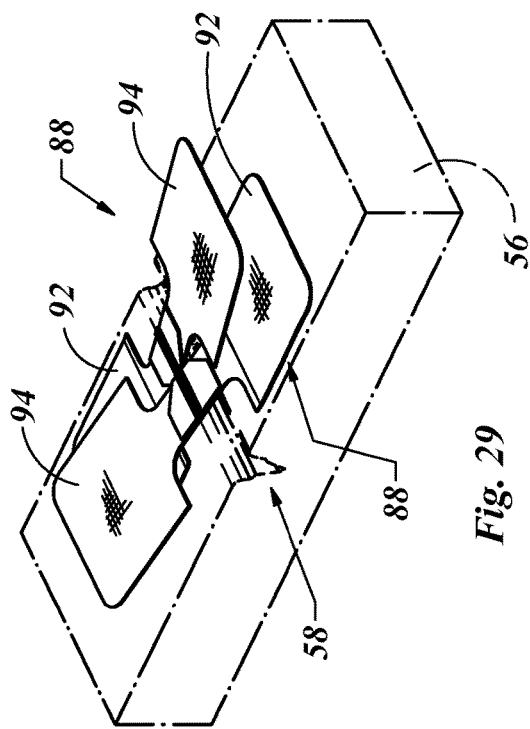
FIG. 29 is a top isometric view of the wound closing bandage of FIG. 26 applied to the skin of a user with an open wound.
Figure 31:
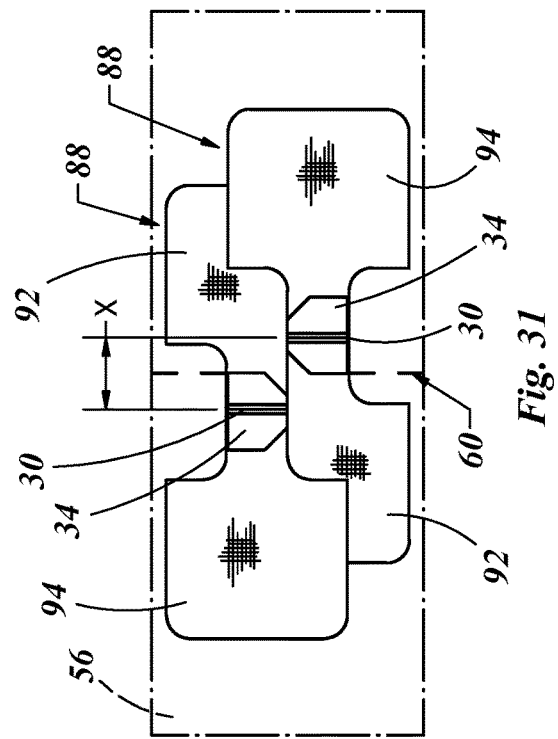
FIG. 31 is a plan view of the wound closing bandage of FIG. 30.
Figure 30:
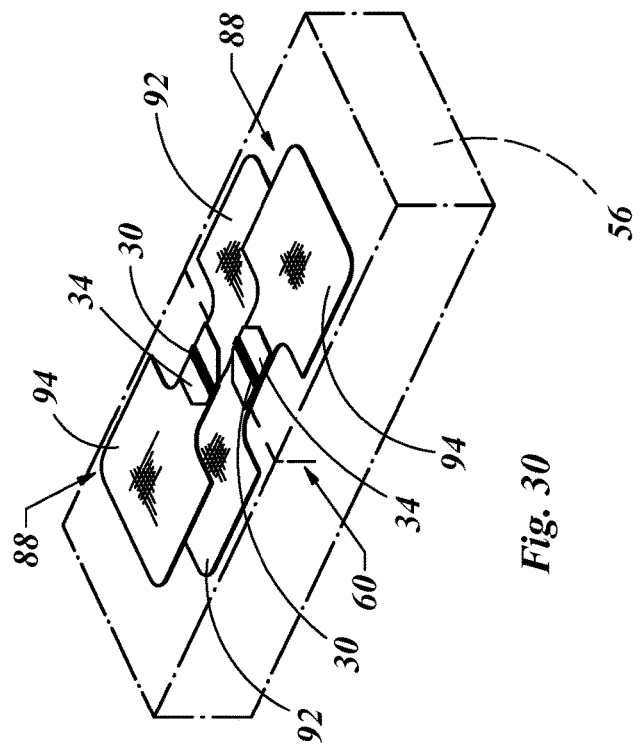
FIG. 30 is a top isometric view of the wound closing bandage of FIG. 29 after the wound closing bandage has close the wound and is secured to the skin.

The use of this version of the wound closing bandage 54" is illustrated in FIGS. 29-31. The first ends 92 may be positioned on the skin 56 on either side of the open wound 58. The second ends 94 may be pulled away from one another to create a closed wound 60. Then the second ends 94 may be secured to the skin 56, partially on the top of the respective first ends 92 already adhered to the skin 56. When the second ends 94 are pulled away from one another, the locator tab 34 may split, half going with each I-shaped member 88, the indicator line 30 may also be split to show a relative distance (x) (FIG. 31) of displacement of the center of each I-shaped member 88 relative to the other. This displacement (x) may be used as general guide with a given distance or may be used in combination with a tension indicator line 86 (not shown in this embodiment) as previously shown and described.

The "I-shaped" members 88 may provide more visibility of the wound 60 as compared to the U-shaped members 62 as previously presented. The U-shaped members 62 may provide a more even pull on the skin 56 at the location of the wound 60. Each may have their advantages and disadvantages as alternative embodiments of the present invention.

The foregoing detailed description of the present invention is provided for purposes of illustration, and it is not intended to be exhaustive or to limit the invention to the particular embodiment shown. The embodiments may provide different capabilities and benefits, depending on the configuration used to implement key features of the invention.

What is claimed is:

1. A wound closing bandage comprising:
a first bandage element and a second bandage element each constructed of an elastomeric material and each with an adhesive backing on one surface thereof, the first bandage element and the second bandage element positioned adjacent to one another such that a portion of the first bandage element overlaps a portion of the second bandage element; and
a locator tab bonded to the first bandage element and the second bandage element and positioned near a center portion of both the first bandage element and the second bandage element, the locator tab maintaining a relative location of the first bandage element to the second bandage element prior to using the wound closing bandage and the locator tab is functionally removed when used as the first bandage element is displaced from the second bandage element.

2. The wound closing bandage according to claim 1, wherein the elastomeric material is a material with a modulus of elasticity between 0.3 and 6.0 MPa.

3. The wound closing bandage according to claim 1, wherein the elastomeric material is comprised of a semipermeable woven material.

4. The wound closing bandage according to claim 1, wherein the first bandage element and the second bandage elements have a reduced section in a center portion of each of the first bandage element and the second bandage element.

5. The wound closing bandage according to claim 4, wherein the reduced section is on one side of each of the first bandage element and the second bandage element so as to create a U-shape.

6. The wound closing bandage according to claim 4, wherein the reduced section is on both sides of each of the first bandage element and the second bandage elements so as to create an I-shape.

7. The wound closing bandage according to claim 1, wherein the adhesive backing on one surface of each of the first bandage element and the second bandage element covers the entirety of the one surface.

8. The wound closing bandage according to claim 1, wherein the locator tab includes a relief, thus providing a reduced section in a location on the locator tab, thereby providing a stress point near the relief when a force is applied to the locator tab.

9. The wound closing bandage according to claim 1, further comprising an indicator line positioned near a center portion of the locator tab.

10. The wound closing bandage according to claim 9, further comprising a tension indicator line on the first bandage element displaced from the locator tab, whereby when a first end of each of the first bandage element and the second bandage element are secured to a surface and a predetermined amount of force is applied to a second end of the first bandage element and the second bandage element, the indicator line on the locator tab will align with the tension indicator line.

11. A wound closing bandage comprising:
two substantially equal bandage element means with a reduced section on one side and constructed of an elastomeric material and with an adhesive backing on one surface thereof, the bandage element means positioned with the reduced section of each substantially equal bandage element means adjacent to one another such that a portion of the first bandage element means overlaps a portion of the second bandage element means; and
a locator tab bonded to the substantially equal bandage element means near a center portion of both the substantially equal bandage element means, the locator tab maintaining a relative location of the two substantially equal bandage element means to each other prior to using the wound closing bandage and the locator tab is functionally removed when used as the first bandage element means is displaced from the second bandage element means.

12. The wound closing bandage according to claim 11, wherein the elastomeric material is a material with a modulus of elasticity between 0.3 and 6.0 MPa.

13. The wound closing bandage according to claim 11, wherein the elastomeric material is comprised of a semipermeable woven material.

14. The wound closing bandage according to claim 11, wherein the reduced section is in a center portion of each of the substantially equal bandage element means.

15. The wound closing bandage according to claim 14, wherein the reduced section is on only one side of each of the substantially equal bandage element means so as to create a U-shape.

16. The wound closing bandage according to claim 14, wherein the reduced section is on two sides of each of the substantially equal bandage element means so as to create an I-shape.

17. The wound closing bandage according to claim 11, wherein the adhesive backing on one surface of each of the substantially equal bandage element means covers the entirety of the one surface.

18. The wound closing bandage according to claim 11, wherein the locator tab includes a relief, thus providing a reduced section in a location on the locator tab, thereby providing a stress point near the relief when a force is applied to the locator tab.

19. The wound closing bandage according to claim 11, further comprising an indicator line positioned near a center portion of the locator tab.

20. The wound closing bandage according to claim 19, further comprising a tension indicator line on each of the substantially equal bandage element means, the tension indicator line displaced from the locator tab, whereby when a first end of each of the substantially equal bandage element means are secured to a surface and a predetermined amount of force is applied to a second end of the substantially equal bandage element means, the indicator line on the locator tab will align with the tension indicator line.

* * * * *